US011696714B2

(12) United States Patent
Aimone et al.

(10) Patent No.: US 11,696,714 B2
(45) Date of Patent: Jul. 11, 2023

(54) SYSTEM AND METHOD FOR BRAIN MODELLING

(71) Applicant: INTERAXON INC., Toronto (CA)

(72) Inventors: Christopher Allen Aimone, Toronto (CA); Graeme Moffat, Toronto (CA); Hubert Jacob Banville, Toronto (CA); Sean Wood, Toronto (CA); Subash Padmanaban, Toronto (CA); Sam Kerr, Toronto (CA); Aravind Ravi, Toronto (CA)

(73) Assignee: INTERAXON INC., Toronto (CA)

( * ) Notice: Subject to any disclaimer, the term of this patent is extended or adjusted under 35 U.S.C. 154(b) by 456 days.

(21) Appl. No.: 16/858,093

(22) Filed: Apr. 24, 2020

(65) Prior Publication Data

US 2020/0337625 A1 Oct. 29, 2020

Related U.S. Application Data

(60) Provisional application No. 62/838,208, filed on Apr. 24, 2019.

(51) Int. Cl.
*A61B 5/246* (2021.01)
*A61B 5/375* (2021.01)
*G16H 50/50* (2018.01)
*A61B 5/377* (2021.01)
*A61B 5/00* (2006.01)

(52) U.S. Cl.
CPC .............. *A61B 5/246* (2021.01); *A61B 5/375* (2021.01); *A61B 5/377* (2021.01); *A61B 5/7267* (2013.01); *A61B 5/7275* (2013.01); *G16H 50/50* (2018.01)

(58) Field of Classification Search
CPC ......... A61B 5/246; A61B 5/375; A61B 5/377; A61B 5/7267; A61B 5/7275; G16H 50/50
USPC ......................................................... 600/544
See application file for complete search history.

(56) References Cited

U.S. PATENT DOCUMENTS

| 11,564,591 | B1* | 1/2023 | Narayan | A61B 5/277 |
| 2014/0223462 | A1* | 8/2014 | Aimone | G16H 40/67 |
| | | | | 725/10 |
| 2019/0113973 | A1* | 4/2019 | Coleman | H04L 12/16 |
| 2019/0387998 | A1* | 12/2019 | Garten | A61M 21/00 |
| 2022/0240846 | A1* | 8/2022 | Howard | A61N 1/36031 |

* cited by examiner

*Primary Examiner* — Michael Tomaszewski
*Assistant Examiner* — Rachael Sojin Stone
(74) *Attorney, Agent, or Firm* — Norton Rose Fulbright Canada LLP

(57) ABSTRACT

Brain modelling includes receiving time-coded bio-signal data associated with a user; receiving time-coded stimulus event data; projecting the time-coded bio-signal data into a lower dimensioned feature space; extracting features from the lower dimensioned feature space that correspond to time codes of the time-coded stimulus event data to identify a brain response; generating a training data set for the brain response using the features; training a brain model using the training set, the brain model unique to the user; generating a brain state prediction for the user output from the trained brain model, and automatically computing similarity metrics of the brain model as compared to other user data; and inputting the brain state prediction to a feedback model to determine a feedback stimulus for the user, wherein the feedback model is associated with a target brain state.

20 Claims, 27 Drawing Sheets

SYSTEM AND METHOD FOR BRAIN MODELLING

CROSS-REFERENCE TO RELATED APPLICATION(S)

This application claims benefit and priority from U.S. Provisional Patent Application No. 62/838,208 filed on Apr. 24, 2019, the contents of which are incorporated by reference herein.

FIELD

This relates to bio-signal collection methods, and systems that utilize bio-signal data.

BACKGROUND

Bio-signals are signals that are generated by biological beings that can be measured and monitored. Electroencephalographs, galvanometers, and electrocardiographs are examples of devices that are used to measure and monitor bio-signals generated by humans.

A human brain generates bio-signals such as electrical patterns. These electrical patterns, or brainwaves, are measurable by devices such as an electroencephalogram ("EEG"). Typically, an EEG will measure brainwaves in an analog form. Then, these brainwaves may be analyzed either in their original analog form or in a digital form after an analog to digital conversion.

Measuring and analyzing bio-signals such as brainwave patterns can have a variety of practical applications. For example, brain computer interfaces ("BCI") have been developed that allow users to control devices and computers using brainwave signals.

SUMMARY

According to an aspect, there is provided a computer-implemented method for brain modelling, the method comprising: receiving time-coded bio-signal data associated with a user; receiving time-coded stimulus event data; projecting the time-coded bio-signal data into a lower dimensioned feature space; extracting features from the lower dimensioned feature space that correspond to time codes of the time-coded stimulus event data to identify a brain response; generating a training data set for the brain response using the features; training a brain model using the training set using a processor that modifies parameters of the brain model stored on the memory, the brain model unique to the user; generating a brain state prediction for the user output from the trained brain model, using a processor that accesses the trained brain model stored in memory, and using a processor that automatically computes similarity metrics of the brain model as compared to other user data; and inputting the brain state prediction to a feedback model to determine a feedback stimulus for the user, wherein the feedback model is associated with a target brain state.

In some embodiments, the brain model is trained from a base brain model that is generated by transfer learning from similar users.

In some embodiments, the method further comprises comparing attributes of users to determine covariance, and based on the covariance, identifying the similar users.

In some embodiments, the time-coded bio-signal data includes time-coded EEG data generated by repeated measures.

In some embodiments, the time-coded bio-signal data includes sensed event related potentials.

In some embodiments, the method further comprises receiving non-bio-signal data, extracting features from the non-bio-signal data, and inputting the features of the non-bio-signal data to train the brain model.

In some embodiments, the brain model includes a representation of a relationship between the time-coded bio-signal data and the non-bio-signal data.

In some embodiments, the non-bio-signal data includes data representative of an environmental state of the user.

In some embodiments, the training of the brain model includes at least one of supervised, semi-supervised, unsupervised learning, or reinforcement learning.

In some embodiments, the brain model is at least one of a logistic regression, linear discriminant analysis, a random forest, gradient boosted trees, support vector machines, or ensemble learning.

In some embodiments, the brain model is a neural network.

In some embodiments, the brain model is trained by training parameters of the neural network.

In some embodiments, the neural network is at least one of or a combination of a convolutional neural network, recurrent neural network or long short term memory network.

In some embodiments, the feedback model is a neural network.

In some embodiments, the brain model is a generator and the feedback model is a discriminator in a generative adversarial network (GAN) framework.

In some embodiments, the feedback stimulus includes environmental effects.

In some embodiments, the method further comprises receiving additional bio-signal data associated with the feedback stimulus, and further training the brain model based at least in part on the additional bio-signal data.

In some embodiments, the method further comprises determining a treatment protocol for a user based at least in part on the trained brain model and the feedback model.

In some embodiments, the method further comprises a treatment algorithm that provides state estimates of the user's brain and behaviour states through inputs received from the brain model, resulting in a treatment protocol stimulus displayed to the user resulting in a brain and behavioural response in the user.

In some embodiments, the user's bio-signal and behavioural state response to the stimulus is measured and used as an additional training input to the brain model, wherein the brain model is trained to reproduce outputs from the therapeutic algorithm from the context vector alone, defining a mapping from the context variables to estimates of desired brain response.

In some embodiments, the method further comprises a diagnostic classification output resulting from the difference between a user's predicted and actual brain and behavioural response to the stimulus.

According to another aspect, there is provided a computer system comprising: a bio-signal sensor in communication with a computing device, the computing device including a processor and a memory in communication with the processor, the memory storing instructions that, when executed by the processor cause the processor to perform a method as described herein.

According to a further aspect, there is provided a non-transitory computer readable medium comprising a computer readable memory storing computer executable instructions thereon that when executed by a computer cause the computer to perform a method as described herein.

Other features will become apparent from the drawings in conjunction with the following description.

BRIEF DESCRIPTION OF DRAWINGS

In the figures which illustrate example embodiments.

DETAILED DESCRIPTION

Embodiments described herein relate generally to computer systems and computer implemented methods for collecting bio-signal and non-bio-signal data, applying data processing to the collected data, and using the collected and processed data.

Bio-signal data of a user, such as brain activity data or brain data, may be represented in the form of a bio-signal model or a brain model, such as a "brainprint" or "brain signature". In an example, a brain model can be a simplification of brain data of a user. In some embodiments, a brain model can be a form of biometric identification associated with a particular user.

In some embodiments, bio-signal data may be used for event-related potential ("ERP") analysis, to measure a user's brain response that is the result of a specific sensory, cognitive, or motor event. The ERP data may be used for the brain model associated with that user.

Figure 1:
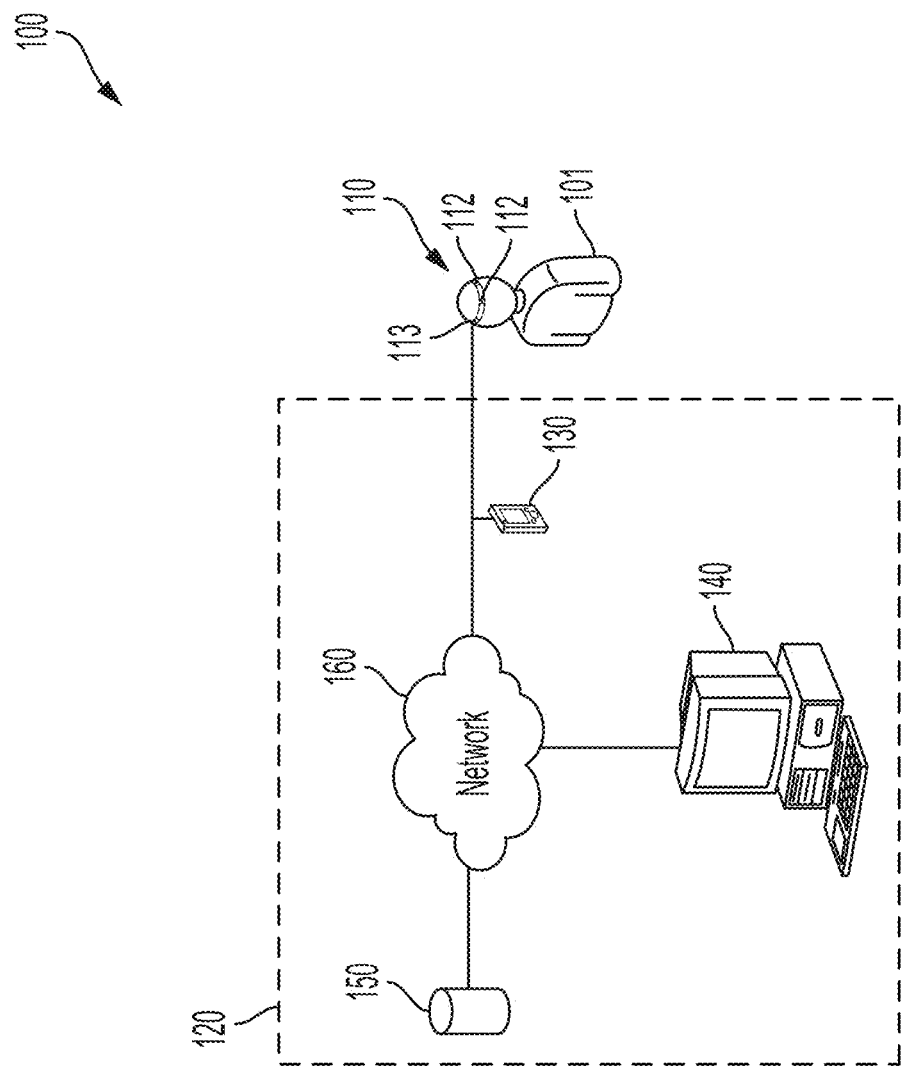
FIG. 1 illustrates a schematic view of an embodiment of a brain model system, according to an embodiment.

FIG. 1 is a schematic diagram illustrating a brain model system 100 for generating a brain model, in an example embodiment.

In some embodiments, system 100 includes a wearable device 110, which may be head-mountable by a user 101, as illustrated. One or more sensors 112 may be disposed on wearable device 110. Sensors 112 can include internal sensors, for example, contained in a computing platform 120, external sensors, for example, external and connected to computing platform 120, and wearable sensors such as disposed on wearable device 110. In some embodiments, sensors 112 may be disposed in contact or adjacent user 101, at a suitable location for sensing relevant data.

System 100 also includes a computing platform 120 connected to sensors 112, in an example, by way of wearable device 110, to receive sensor data from sensors 112. Sensors 112 may be connected to a computing platform 120, for example, a computing device or devices of the trusted local network or mobile computing device, such as a client computing device 130, by wired or wireless connection, such as, for example, USB or BLUETOOTH connections. Client computing device 130 and/or wearable device 110 may be connected to a remote computing device 140 and a sensor data store 150 by way of a network 160.

One or more user effectors 113 may also be provided at wearable device 110 or other local computing device for providing feedback to the user, for example, tactile feedback such as vibrations or providing audio or visual feedback or indications to user 101. In some embodiments, wearable device 110 may include a sound generator such as a speaker to provide auditory feedback to a user. Effectors 113 may be internal or external to computing platform 120.

Sensors 112 include sensors such as bio-signal sensors for sensing bio-signal data, such as from user 101, and/or non-bio-signal sensors for sensing non-bio-signal data, such as from an environment surrounding user 101.

In some embodiments, sensors 112 may include a wearable sensor for collecting biological data, such as a consumer grade EEG headset with one or more electrodes for collecting brainwaves from a user. An EEG using fewer electrodes can make the wearable sensor more affordable to produce, although an EEG with more electrodes can comparatively collect more data, or collect data more accurately.

Non-bio-signal data and bio-signal data (such as EEG data) from multiple users may be collected, processed and analyzed.

Sensors 112 for collecting bio-signal data include, for example, electroencephalogram (EEG) sensors, electrooculography (EOG) sensors, galvanometer sensors, electrocardiograph (ECG) sensors, fNIRS (functional near infrared spectroscopy) sensors, heart rate sensors such as photoplethysmography (PPG).

In some embodiments, sensors 112 for collecting bio-signal data can include eye-tracking sensors tracking types of eye movement, blood pressure sensors, breathing sensors, mouth movement, in-mouth sensors, pedometers, gyroscopes, fMRI, and any other type of sensor. Sensors may be of various types, including: electrical bio-signal sensor in electrical contact with the user's skin; capacitive bio-signal sensor in capacitive contact with the user's skin; blood flow sensor measuring properties of the user's blood flow; and wireless communication sensor placed sub-dermally underneath the user's skin. Other sensor types may be possible.

Many sensor types may be used to obtain data from a user or regarding other properties or events, including, but not necessarily limited to the following: three-axis accelerometers; acoustic; air velocity; gas detectors; humidity sensors; weight scales; infrared camera; magnetic fields; pH level; speed; atmospheric pressure; blood glucose; arterial blood pressure; electrocardiography; temperature; respiratory rate; pulse oximetry; environmental (e.g. thermometer); brain activity measurement devices (e.g. EEG or FNIRS); cardiovascular activity through ECG or pulse oxymetry; muscle activity using EMG; breath measurement using strain sensors; skin conductance; body motion using inertial sensors such as gyroscope and accelerometer; environmental sound (microphone); environmental visuals (video and images); media players; geographical based context; tasked based context; telephone calls; email reading and composition; and internet searching and reading.

Brain activity measurement can include a variety of sensor or input technologies, including EEG, fNIRS, fMRI, TCMS, electroconvulsive, tDCS, and ultrasound. These terms are generally defined as follows.

Adaptive brainstate change notification (ABCN) neurofeedabck, also called neurotherapy or neurobiofeedback, is a type of biofeedback that uses realtime displays of electroencephalography (EEG) or hemoencephalography (HEG) to illustrate brain activity and teach self-regulation. EEG neurofeedback uses sensors that are placed on the scalp to measure brain waves, while HEG neurofeedback uses infrared (IR) sensors or functional magnetic resonance imaging (fMRI) to measure brain blood flow.

fNIRS (functional near-infrared spectroscopy) is a form of neurofeedback (HEG) for the purpose of functional neuroimaging. Using fNIRS, brain activity is measured through hemodynamic responses associated with neuron behavior.

fNIRS is a non-invasive imaging method involving the quantification of chromophore concentration resolved from the measurement of near infrared (NIR) light attenuation, temporal or phasic changes. NIR spectrum light takes advantage of the optical window in which skin, tissue, and bone are mostly transparent to NIR light in the spectrum of 700-900 nm, while hemoglobin (Hb) and deoxygenated-hemoglobin (deoxy-Hb) are stronger absorbers of light. Differences in the absorption spectra of deoxy-Hb and oxy-Hb allow the measurement of relative changes in hemoglobin concentration through the use of light attenuation at multiple wavelengths. In some configurations, fast optical signal scattering patterns of near infrared light may be implemented.

TCMS/TMS is transcranial magnetic stimulation. Transcranial magnetic stimulation (TMS) is a procedure that uses magnetic fields to stimulate nerve cells in the brain.

With TMS, a large electromagnetic coil is placed against your scalp near your forehead. The electromagnet used in TMS creates electric currents that stimulate nerve cells in the region of interest in the brain RTCMS/rTMS is repetitive transcranial magnetic stimulation (rTMS).

tDCS is transcranial direct current stimulation, which is a form of neurostimulation which uses constant, low current delivered directly to the brain area of interest via small electrodes Ultrasound refers to ultrasound waves that are used to effect brain activity.

In some embodiments, one or more sensors 112 may collect non-bio-signal data such as time, GPS location, barometric pressure, acceleration forces, ambient light, sound, and other data.

System 100 includes a computing platform 120 configured to process and analyze collected bio-signal and non-bio-signal data. Processing and analysis of data can be performed on computing platform 120 by hardware, software, or any combination.

Computing platform 120 may be a computing device, a client device, such as client computing device 130, a local server, a remotely located server, such as remote computing device 140, a cloud-based server, a SAAS platform, or some combination thereof. A cloud-based platform implementation may provide one or more advantages including: openness, flexibility, and extendibility; manageable centrally; reliability; scalability; being optimized for computing resources; having an ability to aggregate information across a number of users; and ability to connect across a number of users and find matching sub-groups of interest.

Figure 2:
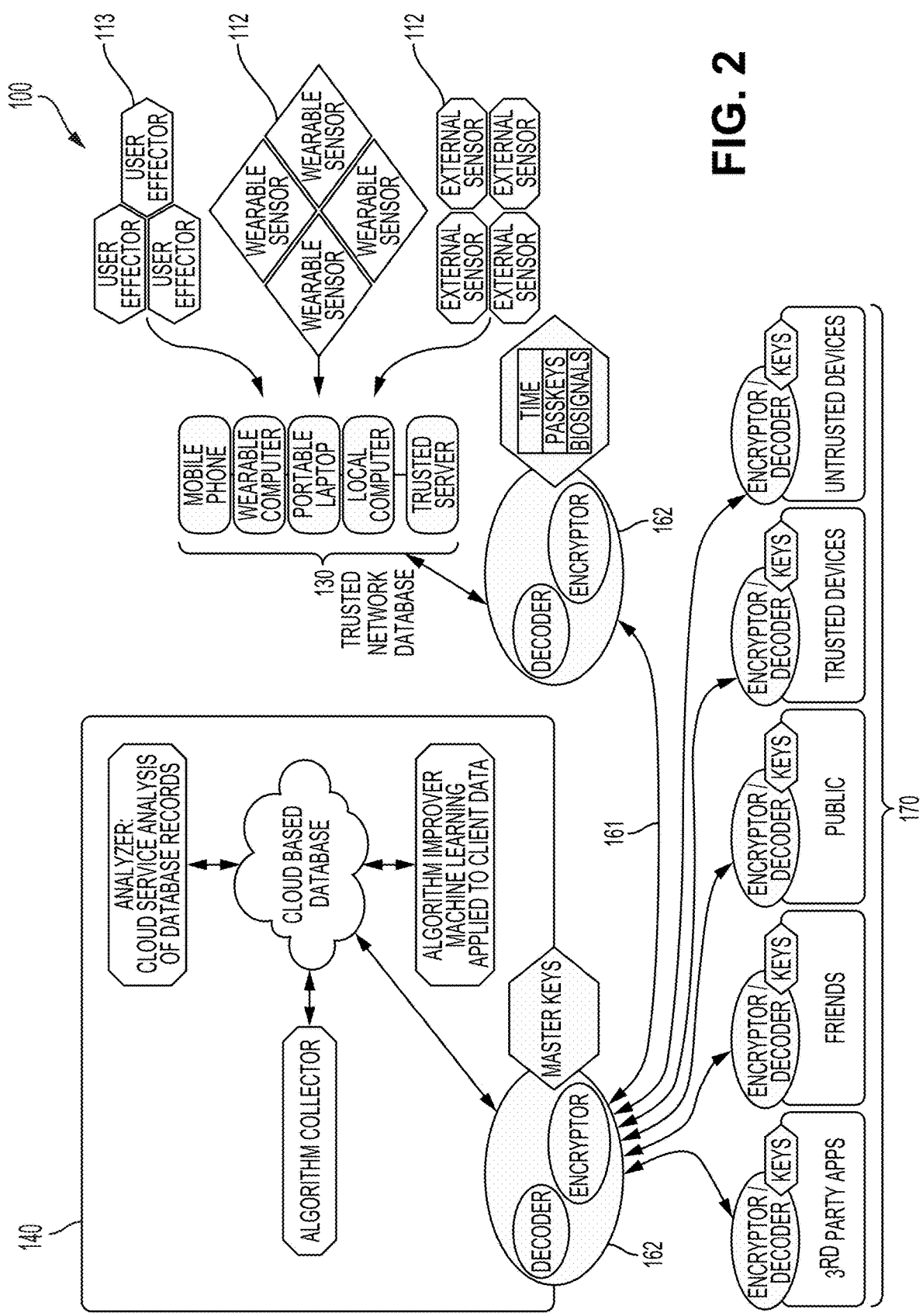
FIG. 2 illustrates an embodiment of a brain model system, including a cloud service model and a local trusted network of client devices, according to an embodiment.

Referring to FIG. 2, in an embodiment of system 100 there is shown a trusted network of local client computing devices 130 and a software as a service (SAAS) platform operating at one or more computer servers such as remote computing device 140. The trusted network of local client computing devices 130 may comprise, without limitation, one or more of the following, in various combinations: a mobile phone, wearable computer, laptop, local computer, or trusted server.

Client computing devices 130 may communicate with the SAAS platform through network 160 or a network connection 161, for example, a wired or wireless connection. The start and end points 162 of the above described connections may be configured to encrypt and decrypt data transmissions using suitable encryption techniques. Non-limiting examples of such techniques can include MD5 or SHA encoding. Additionally, protocols such as secure HTTP (HTTPS) can be used to encrypt the transmission medium.

In some embodiments, the SAAS platform comprises an interface for sharing stored and analyzed user data to other client devices, organizations, or third party applications. As can been seen in FIG. 2 for example, examples of other client devices, organizations, or third party applications 170 can include untrusted devices, the public, friends, trusted devices and third party applications. These devices, organizations, and applications can connect to the system via wired or wireless connections 161, for example over the internet. Furthermore, these connections may also be encrypted/decrypted 162 using similar techniques as described above.

As shown in FIG. 2, in an example embodiment, the SAAS platform may include a cloud based database, an analyzer, an algorithm collector, and an algorithm improver. The cloud based database may store all, or a subset, of the raw data associated with a user profile or received from sensors 112. The database may also store user data that has been pre-processed or analyzed by the client device or devices. Alternatives to cloud-based databases could be used.

Similar to the client device or devices, the analyzer in the SAAS platform may be used to process and analyze raw data collected by internal and external sensors. Additionally, the analyzer may be configured to utilize algorithms stored in the algorithm collector to process and analyze both raw data and user profile data.

In some embodiments, big data pipelines may be implemented for bio-signal analysis. In an example, a split bio-signal pipeline may be implemented such that parts of the pipeline are implemented on a local client computing device 130, such as a mobile device or tablet device, and the remained of the pipeline is served as a platform as a service (Paas) and configured to return predictions, such as for a brain model deployed to multiple people concurrently.

In another example, distributed processing and incremental model building may be used to develop personalized bio-signal models or brain models. In some embodiments, a global model may be built from a cloud database of bio-signal and other data, from which features can be extracted and incrementally added to a model based on user- and session-specific data.

In addition to analyzing data associated with individual users, the analyzer may analyze aggregated data (data associated with one or more users). Aggregate data analysis, may provide insight into brainwave patterns for a particular population. An analysis over a set of users may indicate, that one or more patterns of features as extracted by the feature extractors discussed earlier are associated with a specific mental state for certain types of users.

Thus, system 100 is able to exploit big data collected in the cloud and gather intelligence across a user demographic population.

FOOOF ("fitting oscillations & one over f") is a tool for parameterizing neural power spectra. FOOOF models the power spectrum as combination of two distinct functional processes: (1) an aperiodic component, reflecting 1/f like characteristics, with (2) a variable number of periodic components (putative oscillations), as peaks rising above the aperiodic component.

As shown in study work utilizing FOOOF to parameterize neural power spectra, neural and bio-signal trends across populations of users can be established, and provide predictions based on what group a user session most likely belongs to, for example, on the basis of age, alcohol consumption, circadian cycle, or other suitable group category.

Figure 8:
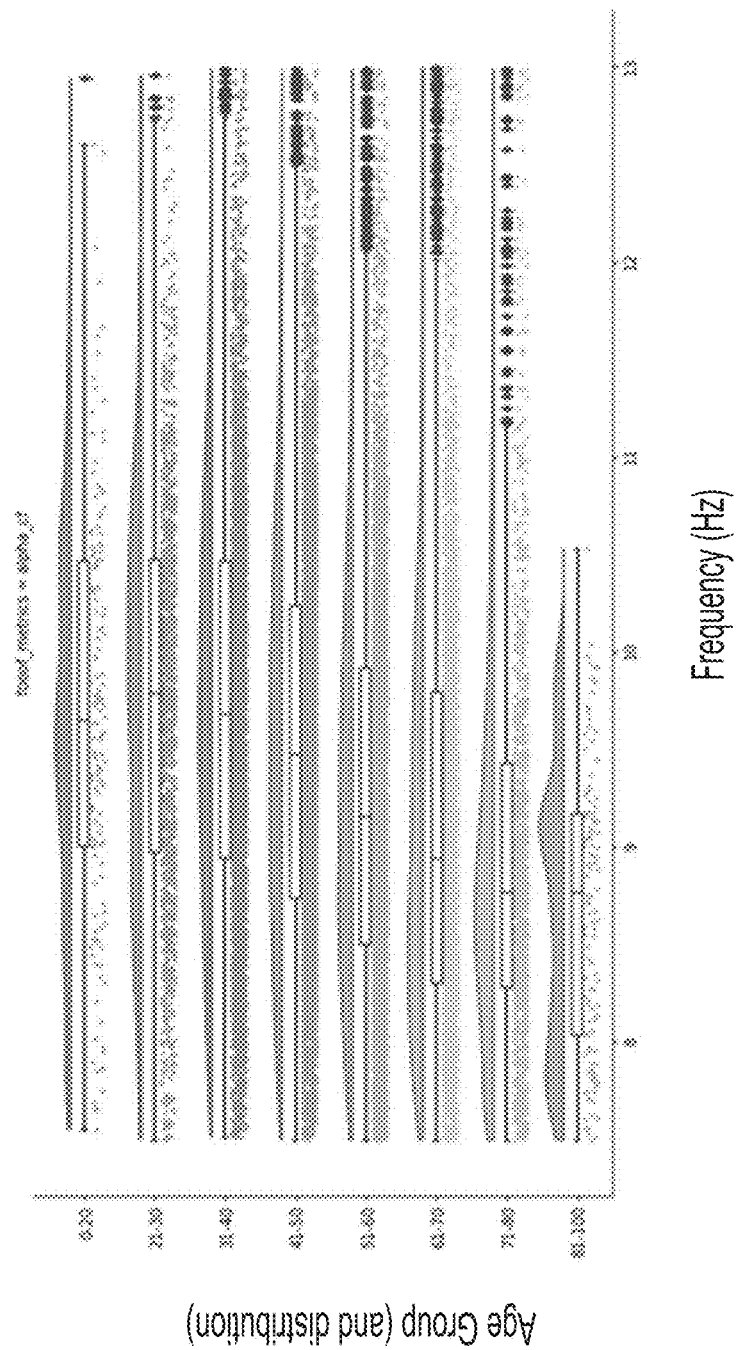
FIG. 8 illustrates a multidimensional histogram of alpha center frequency for an aggregate of users, according to an embodiment.

FIG. 8 illustrates a multidimensional histogram of alpha center frequency for an aggregate of a number of different users, grouped by age and illustrating the distribution. FIG. 8 illustrates how alpha center frequency changes with age.

In one example embodiment, the analyzer may utilize a machine learning algorithm stored in the algorithm collector to identify and correlate patterns with specific types of users. These algorithms, for example, may identify patterns common to many users. More than one machine learning algorithm can be stored in the algorithm collector and multiple algorithms may be supplied to the analyzer depending on the circumstances. Another embodiment might allow third party applications or other parties to supply their own custom algorithms into the algorithm collector so that the custom algorithm may be used by the analyzer.

The analysis results can be used by an algorithm improver to improve the algorithm for future analysis. For example, analysis of the data may uncover different brainwave patterns for different classes of users that may correlate with specific physical or emotional states. These patterns can then be used to update the algorithms so that these patterns are used in the analysis of data collected in the future. There may be correlations found between specific groups of users with a specific set of characteristics. These correlations may be used to improve the performance of the analyzer, algorithm collector, or algorithm improver, or other aspects of the systems or methods.

Improving the algorithms may also comprise a feedback mechanism to allow users of the system to judge the correctness of the analysis. That is, a feedback process may be used to allow the user to evaluate or supervise the machine learning. This feedback mechanism, in an example embodiment, can be a part of the algorithm improver. For example, a user of the client device may be asked whether a particular analysis corresponds with a particular emotion or physical movement experienced at the time the bio-signal and non-bio-signal data was collected. This can be useful where there is more than one pattern for a known physical or emotional state. The feedback mechanism may allow supervisors to review the aggregate data analysis for correctness. The feedback mechanism may allow supervisors to tune the aggregate data analysis algorithm to identify and ignore aberrant data.

The algorithm improver may be used to re-analyze the data. This re-analysis can both validate and improve the analysis algorithms. The algorithm improver may first update the analysis algorithm in the algorithm collector. The data may then be re-analyzed by the analyzer using the updated algorithm stored in the algorithm collector. Also, algorithms on the client device or devices may be updated over the connection 161 by the SAAS platform. The algorithms may be improved through machine learning applied to collected data either on-board the client device or on the server. EEG data may be saved along with application state to allow a machine learning algorithm to optimize the methods that transform the user's brainwaves into usable control signals.

Processing and analyzing of collected data, such as bio-signal data and non-bio-signal data, may be implemented in computer software or hardware at the at least one client device and at least one computer server. A combination of hardware and/or software may be referred to as a "system platform". Reference to the term "cloud" or "cloud server" is intended to refer to at least one computer server. While embodiments and implementations may be disclosed herein in particular non-limiting examples with respect to use of the cloud to implement aspects of computing platform 120, it is understood that a local server, a single remote server, a SAAS platform, or any other computing device may be used instead of the cloud.

Any functions performed by one or more client computing devices 130 could also be performed by the SAAS platform. Raw data collected from internal and external sensors may be sent directly to the SAAS platform for processing, analysis, and storage. However, bandwidth limitations, may require that at least some of the processing and analysis is performed on the client device(s) prior to transmission to the SAAS platform.

The SAAS platform may also be used to perform computationally complicated or expensive tasks that may not be performed as efficiently or effectively on the client device or devices. Furthermore, the SAAS platform may be used to store user data for many users. Since it can store data for many different users, the SAAS platform may also analyze data associated with one or more users. This aggregate data analysis may be used, for example, to determine recurring patterns for various groups of users.

In some embodiments, a combination of hardware and software that that performs processing and analyzing may take the form of a distributed computing architecture such as a mesh network. In a mesh network, network nodes may connect directly, dynamically and non-hierarchically to any or all of the other nodes in the network. A mesh network may be a highly distributed, redundant network. A mesh network may have some nodes connected to each other, or all nodes connected to each other as a fully connected network. The nodes can communicate using a mesh networking protocol.

In an example, nodes of a mesh network may include at least one client device, or network of local client devices, and at least one computer server such as a local server, a remote server, or SAAS platform. Nodes may be wired or wireless. In some embodiments, one or more wireless nodes may form a wireless mesh network. In some embodiments, one or more of the nodes may be wired to another. Any of the processing and analysis of data as described herein may be performed at or by any or all of the nodes of a mesh network. Conveniently, mesh networks may be more robust than a hub-and-spoke network. For example, if a node breaks down, other nodes can automatically reroute transmissions around it.

Each time analysis or processing of user bio-signal data (such as brain data) is performed, an instance of aspects of computing platform 120 may be may be generated by computing platform 120, initiated at either the client device or the cloud, in order to analyze the user's private bio-signal data using particular analysis or processing parameters applied during the analysis or processing. For simplicity, such an instance may be referred to as a "pipeline". Each instance of the pipeline may have an associated pipeline identifier ("ID"). Each pipeline may be associated with a particular activity type, user, bio-signal type of a particular user, application, or any other system-related data. Each pipeline may maintain particular pipeline parameters determined to analyze the user's bio-signal data in a particular way, consistent either with previous analysis of the particular user's bio-signal data, consistent with previous analysis of one or more other user's bio-signal data, or consistent with updated data at the cloud server derived from new or updated scientific research pertaining to the analysis of bio-signal data. Pipelines and/or pipeline parameters may be saved for future use at the client computing device or at the cloud.

Computing platform 120 may preprocess the raw collected biological and non-biological data. This can involve, as non-limiting examples, noise filtering and interpolating gaps in signals, and/or any other solution for handling issues related to signal collection and transmission.

Computing platform 120 may use preprocessed data to extract features from a signal. For example, this may be done by projecting the EEG signal into a lower dimensioned feature space. This projection may aid in the classification of the collected data, for example, by increasing the separability of classes.

Computing platform 120 may classify extracted features of data. Classification may provide an indication of the mental state of the user, such as a meditative state. Various algorithms can be used to classify the features determined in previous stages. For example, a minimum mean distance classifier or a K nearest neighbours classifier may be employed to analyze the data.

Feature extraction and classification may be performed by machine learning systems of computing platform 120. Supervised and/or unsupervised machine learning systems and methods may be employed to improve the accuracy of the steps of feature extraction and classification.

Figure 3:
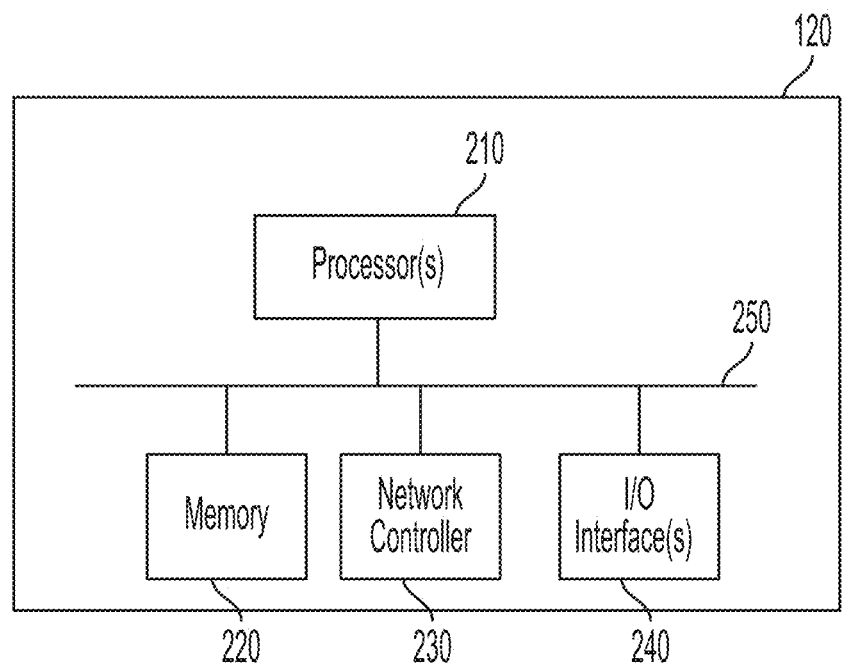
FIG. 3 illustrates is a block diagram of example hardware components of a computing device of the brain model system of FIG. 1, according to an embodiment.

FIG. 3 is a high-level block diagram of a computing device, exemplary of computing platform 120 of system 100. Computing platform 120, under software control, may be used for generating, managing, updating, and utilizing a brain model.

As illustrated, computing platform 120, a computing device, includes one or more processor(s) 210, memory 220, a network controller 230, and one or more I/O interfaces 240 in communication over bus 250.

Processor(s) 210 may be one or more Intel x86, Intel x64, AMD x86-64, PowerPC, ARM processors or the like.

Memory 220 may include random-access memory, read-only memory, or persistent storage such as a hard disk, a solid-state drive or the like. Read-only memory or persistent storage is a computer-readable medium. A computer-readable medium may be organized using a file system, controlled and administered by an operating system governing overall operation of the computing device.

Network controller 230 serves as a communication device to interconnect the computing device with one or more computer networks such as, for example, a local area network (LAN) or the Internet.

One or more I/O interfaces 240 may serve to interconnect the computing device with peripheral devices, such as for example, keyboards, mice, video displays, and the like. Such peripheral devices may include a display of the computing device. Optionally, network controller 230 may be accessed via the one or more I/O interfaces.

Software instructions are executed by processor(s) 210 from a computer-readable medium. For example, software may be loaded into random-access memory from persistent storage of memory 220 or from one or more devices via I/O interfaces 240 for execution by one or more processors 210. As another example, software may be loaded and executed by one or more processors 210 directly from read-only memory.

Example software components and data stored within memory 220 of knowledge distillation system 100 may include software components described below with reference to FIG. 4, and operating system (OS) software (not shown).

Software in memory 220 may generate brain models, and perform methods or processes as described herein.

Figure 4:
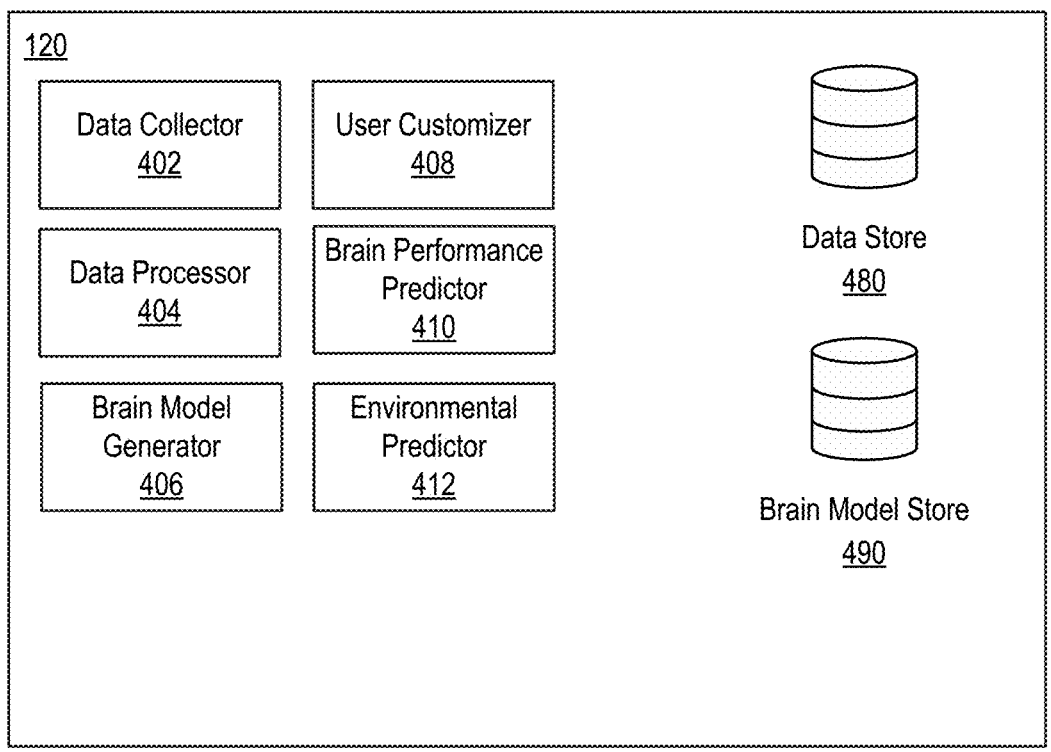
FIG. 4 illustrates the organization of software at the computing device of FIG. 3.

FIG. 4 depicts a simplified organization of example software components and data stored within memory 220 of computing platform 120. As illustrated, these software components include a data collector 402, a data processor 404, a brain model generator 406, a user customizer 408, a brain performance predictor 410, an environmental predictor 412, a data store 480 and a brain model store 490. It will be appreciated that while these components are described as being implemented as software and/or hardware in computing platform 120, such as a combination of local computing device and remote computing device 140 as an SaaS platform, techniques described herein may be embodied in any suitable software and/or hardware configuration.

Data collector 402 receives data such as sensor data, for example, from sensors 112 of system 100. Sensor data can include bio-signal data and non-bio-signal data. Data collector 402 can also receive other data, such as from a client computing device 130 and can include environmental data such as date, time and location information.

Data, such as bio-signal data, non-bio-signal data, and stimulus event data, may be time-coded, for example, encoded with a time stamp.

Data may also be associated with a user, in an example, containing meta data identifying a user from which bio-signal data has been sensed.

Sensor data and other data can be stored in data store 480.

Figure 14:
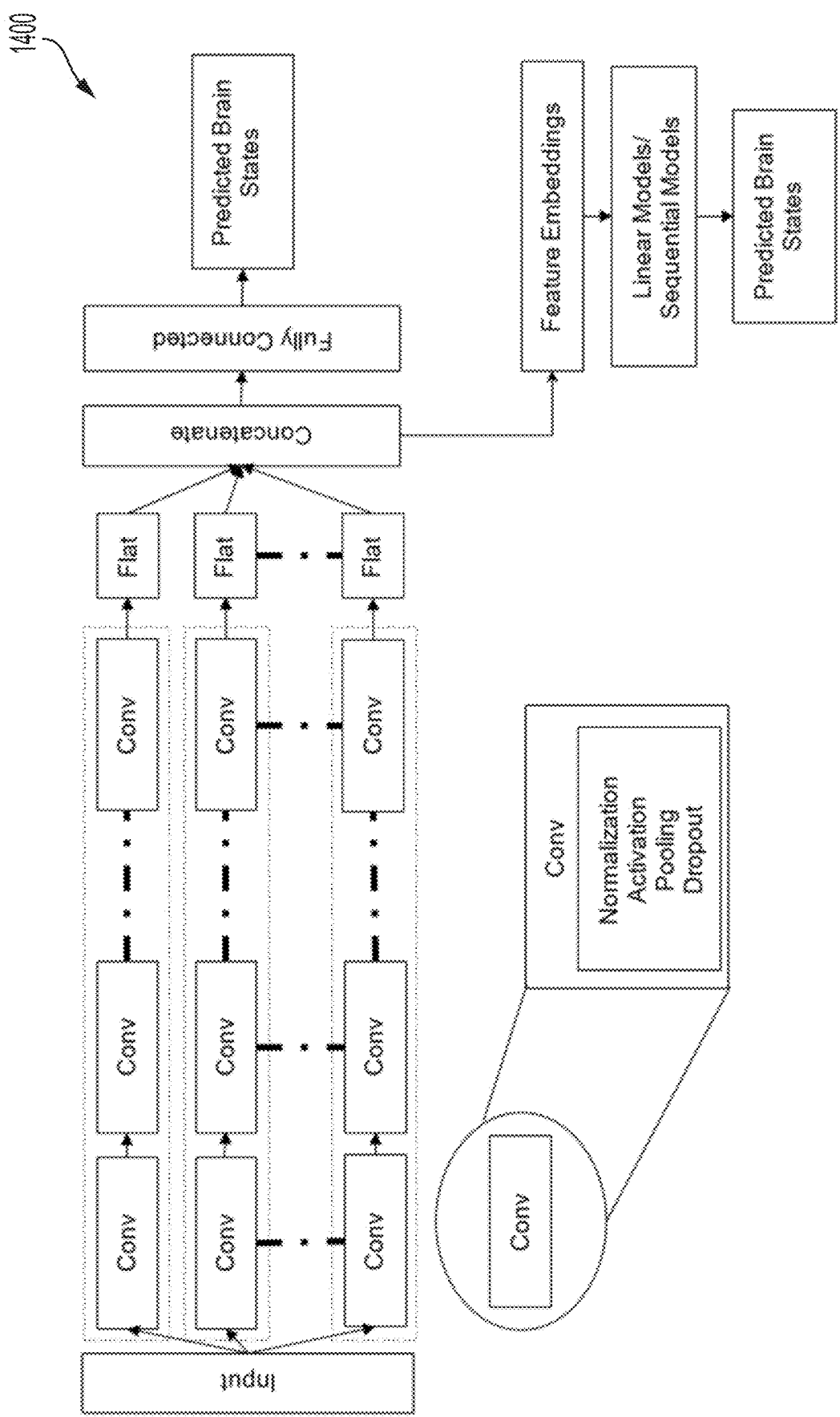
FIG. 14 illustrates a deep learning technique based on convolutional neural networks (CNN) for predicting brain states, according to an embodiment.

Data may be obtained from a variety of sources of data, and data from multiple sources can be leveraged to develop a brain model. As an example, a brain model may be developed that is capable of predicting the different states of sleep. The data used in the process of development can involve the use of user-specific overnight sleep data, publicly available annotated external data, in-house expert labelled sleep data and/or user-identified data. Example sources of data, such as external data, labelled user data, unlabelled user data, and user data labeled by a user, are explained in detail below. With sufficient amount of labelled data, the model development can involve the use of deep learning/machine learning techniques leveraging supervised, semi-supervised or unsupervised training methods. Based on these techniques, a generalized base model that works across multiple users can be developed. One such model developed based on supervised deep learning methods is illustrated in FIG. 14 and described below. FIG. 14 illustrates a deep learning technique based on convolutional neural networks (CNN) for predicting brain states, in particular, different stages of sleep.

Figure 9:
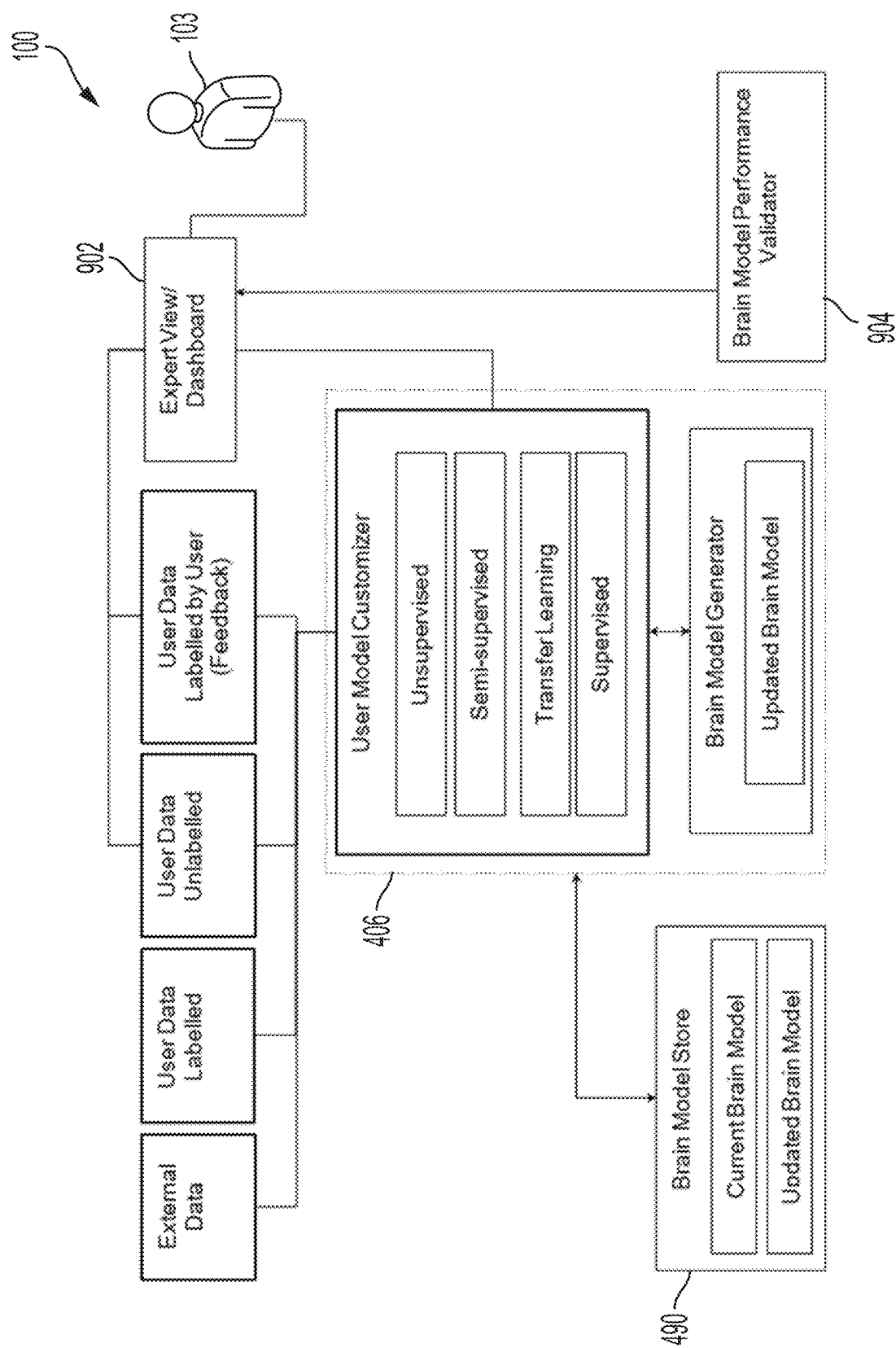
FIG. 9 is a schematic of a system for brain model generation, according to an embodiment.

FIG. 9 is a schematic diagram of the use of various sources of data, including external data, labelled user data, unlabelled user data, and user data labelled by a user for use by brain model generator 406, including a brain model generator and user model customizer. Brain model store 490 can be used to store a current brain model and an updated brain model.

An expert-view/dashboard 902 may be utilized by an expert 103 to allow for offline algorithm validation and development and online improvement/modulation of user experience in real-time, as described in further detail below and with reference to FIG. 12. In some embodiments, an expert-view/dashboard 902 is also in communication with a brain model performance validator 904, which may be configured to verify a brain model's performance in the field, as described in further detail below.

External data can include publicly available annotated bio-signal datasets relevant to a particular task can be leveraged to train a brain model for that specific task. For example, datasets such as the SleepEDF dataset, MASS dataset, and the like, contain annotated overnight sleep recordings with the various states of sleep identified by a sleep expert. A sleep state prediction model can be trained with this dataset as a base model, for example, by brain model generator 406. Further improvements or customizations to the base model can be made with additional amounts of labelled data using techniques such as semi-supervised learning or transfer learning, for example, by the user model customizer.

User testing may be performed on a user such as user 101 to gather labelled training data. Labelled user data can include data collected on users can be labelled by subject matter experts or developers knowledgeable in the domain. For example, subject matter experts in sleep staging can identify the various sleep stages from overnight sleep data collected using the proposed system. This labelled dataset can be used to develop a base model using the proposed methods and further fine-tune or customize to each user, for example, by the user model customizer.

Unlabelled user data can include user data accumulated by system 100 and stored in data store 480. Such data may be initially unlabelled and not annotated with the relevant brain states. This data may require further annotation to extract task relevant features to develop a brain model. In such cases when labelled data is unavailable, a brain model can be developed using unsupervised methods to identify meaningful clusters in the data, for example, using the brain model generator and the user model customizer. This data can also be made available to subject matter experts for annotating the different sleep states.

User data labelled by user can include data identified by the user to different states relevant to a given session via a feedback mechanism provided in the user facing interface in the user equipment. Examples of feedback interface can include, but not limited to, questionnaires, journal entries, behavioral tasks such as tapping/pressing a button, blinking of eyes, etc. These entries can serve as annotations to label the user-data. As an example, if a user performs an ERP session at the end of the day and reports in the journal entry of being 'tired/fatigued.' Then this information can be used to model the user's brain responses into categories such as 'normal', 'alert', 'tired/fatigued'. Another example could involve a journal entry at the end of a full night's sleep in which a user reports of being 'refreshed' or 'fatigued'. Then this could aid in modelling the relationship between an overnight's sleep with the outcome of that night's sleep.

Data collection allows creation of models and general foundation algorithms that can seed and stabilize the user specific classification and adaptation methods. A growing collection of EEG data in user profiles from increasing number of apps and users stored in system 100 can allow further enhancements to generalized pipelines.

Data that is gathered, for example through app usage of a client computing device 130 local to a user, may be combined with other sources of data (biological data and non-biological data such as: behavioural information, demographic information, answers to surveys or formal questionnaires other user entered text) and can be used to do cross-population studies for the refinement of generalized algorithms across a large number of users and may be fine-tuned to specific demographics or based on characterization of brain types using EEG signal analysis of users doing prescribed exercises (for example, experienced meditator versus novice). Anticipated refinements would yield higher performance, quicker adaptation, and greater consistency across the user spectrum.

Data collector 402 may be configured to receive repeated measures. Repeated measures are measurements taken over multiple points of time. Repeated measures may be detected multiple times over a pre-defined time interval. In one example, repeated measures may be ERPs.

A repeated measure may not necessarily mean the same measurement detected, but instead, repeating the same test or prompt multiple times, which may result in different readings each time from the same repeated measure, e.g., how high can a user jump today. Thus, the values may change, but the measurement of that variable is repeating.

Repeated measures over different timescales may be used for revising brain models. This may be achieved by analysis of timestamped EEG signals and activity.

Selection of intervals/repeated measures may depends on the situation. For example, when learning to swing a golf club, a user may improve over half an hour, and could also improve over longer time scale—year or two. The brain model may be updated and revised over each appropriate time scale, while tracking events at repeated measures.

In some embodiments, time-coded feature event data, or stimulus events, may also be acquired, and can provide contextual data for use by system 100.

Collection of contextual data by data collector 402 can aid significantly to the modelling of brain function. Contextual data can take many forms. Contextual data may be data related to another bio-signal such as cardiac function through ECG or PPG. Contextual data can include data related to body temperature, muscle tone, eye movement, and skin impedance.

Additional signals may serve to enhance the ability of system 100 to characterize a user's neuro-physiological state. Other information about a user's context can be collected, such as: the user's goal or intention; the goals or intention of another human they are influenced by; sounds in the environment; changes in scenery or lighting; time of day, electromagnetic waves; ambient temperature; actions or behaviors elicited by the user. Such factors may have an influence on the user's state.

Contextual data may be aggregated in the form of a brain model, and in a time-coded fashion, such that relationship between bio-signals, other physical or behavioural measures obtained from the user and the context may be understood and codified.

Contextual data can be acquired in many ways, including from other sensors; computing devices connected via a network; entered manually, acquired automatically from another person's brain model; or another predictive model or system.

Data collector 402 may be configured to perform time stamping to identify date and/or time information for certain events or features of bio-signal data or non-bio-signal data, such as that received from sensors 112.

Time coding may present various problems. For example, certain sensors 112 or pipelines may generate data that has some temporal uncertainty with regards to when exactly certain events happened. In some embodiments, data collector 402 thus encodes a value representing uncertainty in time. Quantization of time may be performed with coarseness based on uncertainty. The uncertainty window/confidence interval may be in the time stamp record.

Different data sources may have timestamps or be generated from timing mechanisms that are unsynchronized. System 100 may synchronize clocks by having components of system 100 send times back and forth until an adequate estimate of the network delay can be estimated and then data collector 402 can estimate the clock difference (for example, by NTP or computation the round-trip delay time and the offset). Given a history of clock offset measurements between two computers, the timestamp of a remotely collected sample can be remapped into the mutual time domain.

In some embodiments, system 100 may not have a way of keeping time, and data collector 402 may perform synchronization later based on information in the signal (for example where there is EEG data of a user's blinking and video data of the user's face with blinking is also provided, data collector 402 may sync the video to the EEG data).

In the even that non-uniform sampling or missed samples occur, missed samples may be fixed using packet numbers, if they exist, otherwise advanced methods may be used. In some cases, like where data has chunks missing, a computation of a simple time shift use Euclidean distance over the time series may be utilized. Computation of time shift may be done by doing window based Euclidian distance minimization, using cross correlation. Subdivision methods may be used to narrow into finer timescales.

In more difficult cases of non-uniform sampling, data collector 402 may use dynamic time warping (though other methods are possible). A dynamic time warping ("DTW") algorithm may calculate the distance between each associated pairs of two sequences in order to minimize the distance. To manipulate this algorithm, dynamic programming is applied to find the least expensive path through a cumulative distance matrix.

For multi-dimensional data, data collector 402 may use multidimensional dynamic time warping ("MM-DTW"). This pipeline utilizes all dimensions to obtain the optimal path and aligns multiple signals simultaneously. After alignment, the regular similarity measurement can be used to these aligned signals.

In some embodiments, data collector 402 is configured to measure bio-signal data, received from sensors 112 and associated with a stimulus event.

Figure 10:
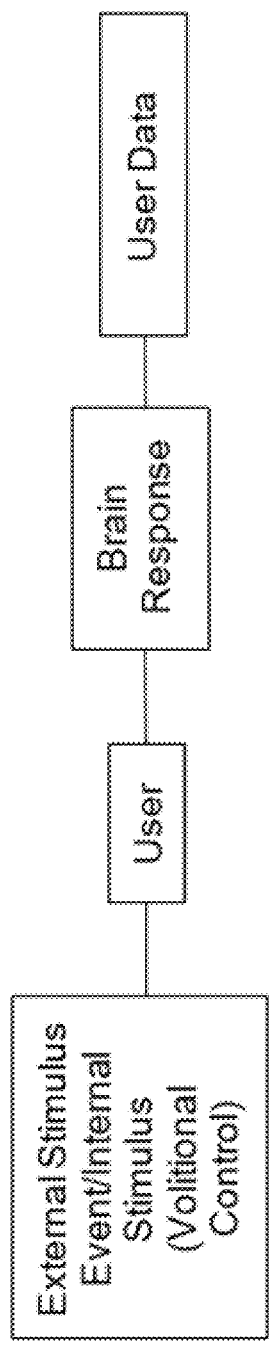
FIG. 10 illustrates a flowchart for a stimulus and brain response, according to an embodiment.

FIG. 10 illustrates a flowchart for a stimulus generated by system 100, and a user's brain response to the stimulus detected, generating user data. The stimulus can be an external stimulus even or an internal stimulus (volitional control). In an example, the stimulus can be an auditory stimulus or mental imagery. A brain response, such as event-related potential (ERP), is detected by system 100, for example, by way of sensors 112, in the form of user data.

In some embodiments, bio-signal data may be associated with a stimulus event with high-precision timing (10 ms or better). The onset of a stimulus event causes system 100 to register and record the onset time, duration, offset time, and other characteristics of the stimulus event in a data stream that is synchronized with the bio-signal data stream. Synchronization of bio-signal data and stimulus event data may allow for more accurate correlation of bio-signal data as a response to a stimulus event.

Synchronization may be done using a variety of techniques. In an example, synchronization may be performed using a token. In another example, synchronization may be performed using common synchronized clocks.

In another example, a camera (such as a forward facing camera of a mobile device) may detect a user's eye blinking, and determine synchronization between a video of the user's eyes and depolarization of EEG and ECG signal as way of synchronization of time stamps.

In another example, synchronization may be done by a user clapping their hands to synchronize audio and video, and used to collect data. Similarly, finger tapping or other tactile actions such as bumping phones or a wall, may be used to synchronize data.

In some embodiments, the stimulus event is an event such as a light, sound, display, mechanical action, chemical reaction, release of volatile chemicals, or electrical stimulus received by or applied to the user, which is under the control of a processing unit that is in connection to the processing unit.

In some embodiments, the stimulus event is in connection to a second processing unit that is not in connection with the first one or more processing unit described above.

In some embodiments, the stimulus event is an event occurring in the user's surroundings, including visual or auditory events, speech, social cues or events from humans or other animals, directed at the user.

In some embodiments, the stimulus event is an event occurring in the user's surroundings, including visual or auditory events, speech, social cues or events from humans or other animals, not directed at the user.

In some embodiments, a bio-signal of interest is measured, for example, by one or more sensors 112, continuously and stimulus event information is recorded in a manner which allows the resynchronization of the events for analysis.

In some embodiments, a bio-signal of interest is not recorded continuously, but recording of the bio-signal is initiated by the onset of a stimulus, in which the processing unit which generates the stimulus is in connection with the bio-signal-processor combination and sends a signal to initiate bio-signal capture for a finite amount of time.

In some embodiments, the duration of bio-signal recording is determined by the stimulus characteristics.

In some embodiments, the duration of bio-signal recording is fixed.

In some embodiments, the duration of recording is determined by the processing unit as defined above, which receives information about the signal from a separate processing that evaluates and relays the characteristics of a stimulus event, whether that stimulus event is generated by a processing unit or is a characteristic of the surrounding environment of the user.

In some embodiments, a subset of a plurality of similar sensors 112 is selectively activated based on the characteristics of the stimulus event (eg. occipital EEG for visual events, temporal EEG for auditory events, sensory integration areas of cortex for multisensory events).

In some embodiments, a subset of a plurality of similar sensors 112 is selectively activated for stimuli which temporally co-occur, whether stimulus onset is synchronous or asynchronous. (e.g. occipital EEG for visual events and temporal EEG for auditory events when those events co-occur.)

In some embodiments, derivatives of bio-signals captured for co-occurring stimulus events are used to subtract brain activity corresponding to one stimulus event from brain activity corresponding to a separate, co-occurring stimulus event.

In some embodiments, a bio-signal recording's time information is reset to a specific value (eg. 0:00.00 s) at the onset of a stimulus.

In some embodiments, stimulus events detected by the system in are used to inform a separate instantiation of said system used by a separate user in visual or auditory proximity to the original user.

In some embodiments, stimulus events detected by the system are used to inform a separate instantiation of said system used by a separate user in physical contact with the original user.

In some embodiments, stimulus events detected by the system are used to inform a separate instantiation of said system used by a separate user in remote connection with the original user.

In some embodiments, bio-signal events detected by the system are used to inform a separate instantiation of said system used by a separate user in visual or auditory proximity, physical contact, or remote connection to the original user.

Data processor 404 may be configured to process data acquired by data collector 402, in an example, to a format suitable for generating a brain model.

As noted above, user testing may be performed on a user such as user 101 to gather labelled training data. With control of the experimental conditions, computing platform 120 can map the basic sources of variation to determine the general signal characteristics of target brain states of interest.

Brain states of interest can include emotional states, as well as the intensity of those emotional states. In an example, an emotional state can be a state of arousal, or a state of high arousal and high intensity emotion. An emotional state may occur when a user is emotionally triggered, and the user may respond in a way such that is difficult for the user to return back to a lower intensity, or "base" emotional state. This type of reaction may occur in user's who suffer from PTSD, or when in an intense argument.

Brain states may be associated with states of attention, and are of interest in certain fields such as in the practice of meditation, a user engaged in an educational scenario, or when a user is in communication with others.

Brain states may also be associated with sleep states. Sleep states can be important for health applications, or for technological applications such as a "do not disturb" mode that is activated automatically on a device, such as a user's mobile device, that disables or enables certain features of the mobile device or in the user's environment when a particular brain state (such as a sleep state) is detected.

Bio-signal data may be mapped to brain states through labelling approaches such as expert labelling, self labelling, consensus labelling, and distribution mapping. Direct unsupervised or self-supervised machine learning can also be used to identify potential brain states of interest automatically, by labelling structure in the data. The meaning of this structure in the data may be discovered at a later stage, or may become part of a system's functioning (such as: as a predictor), even without a full understanding of the meaning of the brain state.

Machine learning techniques may also be used to automatically map bio-signals to target brain states, using supervised learning methods provided from labeling approaches.

Data processor 404 may be configured to process bio-signal data and non-bio-signal data before it is used to generate a brain model. In an example, data can be filtered, normalized and cleaned to remove artifacts with blind source separation or regression techniques; features or relevant representations of the data can also be extracted from the data to simplify the task of generating the brain model.

In some embodiments, data can also be used as is, for example when the brain model is an end-to-end neural network, in which case the preprocessing and feature extraction steps are implicitly learned by the neural network during its training.

Data processor 404 may receive feature event data (including identifications of feature events, and respective values), which may be inputted manually by a respective user, or may be sourced from elsewhere, such as from a calendar application or emails accessible from the client computing device pertaining to the user.

Feature event data can be used as a point of reference during the development or training of the brain model. Feature event data can act as ground truth or correlate, to which the bio-signal/non-bio-signal data is compared. This way, statistical associations between the patterns found in bio-signal/non-bio-signal data and the feature events can be uncovered. Once these patterns are identified and recognizable by the brain model, for example by using statistical tests or predictive machine learning models such as neural networks, it may become easier to understand the behaviour or mental state of the user. As an example, the relationship between the bio-signals and the time of the day can be included into a brain model.

For analysis purposes by system 100, it may be significant that the feature events occur together usually in a point in time or occur together at a place. Therefore, the feature event data may be time-coded, optionally by data processor 404, in order to reference against bio-signal and/or non-bio-signal data of the user with the same or similar time codes. A feature event is all of the variables that go into getting a single data point of multiple variables. Features can be derived from any measure or variable that is available to system 100, such as time of day, EEG signal, heart rate, person's mood, age, gender, height, weight education, income, etc.

Feature events may be maintained in a database in data store 480. To perform predictions, data processor 404 identifies matching patterns and uses the highest order feature events first to do the classification.

Such feature event data may be used to generate and revise brain models, as described below.

Brain model generator 406 receives data from data collector 402 and data processor 204, and is configured to generate a brain model or a bio-signal model, as described herein.

Generated brain models may be stored in brain model store 490.

A brain model may be broadly defined as a representation of brain data. In some embodiments, a brain model is a framework or structure of brain data. A brain model may also include representations of other bio-signal data and non-bio-signal data.

In some embodiments, a brain model can form part of a user profile associated with a user.

In some embodiments, a brain model may reflect bio-signal data generated in the responses of a user to a task or selection of tasks provided to the user.

A brain model may be used to predict a brain state of a user, an emotional state or a measure of arousal or a behaviour. In some embodiments, a brain model may provide insights into what a user might do next.

In some embodiments, a brain model is generated to learn a relationship between an external/internal stimulus event and a brain response. Data representing a brain response can be represented as a function of a stimulus event, whereby the function is a brain model.

Figure 13:
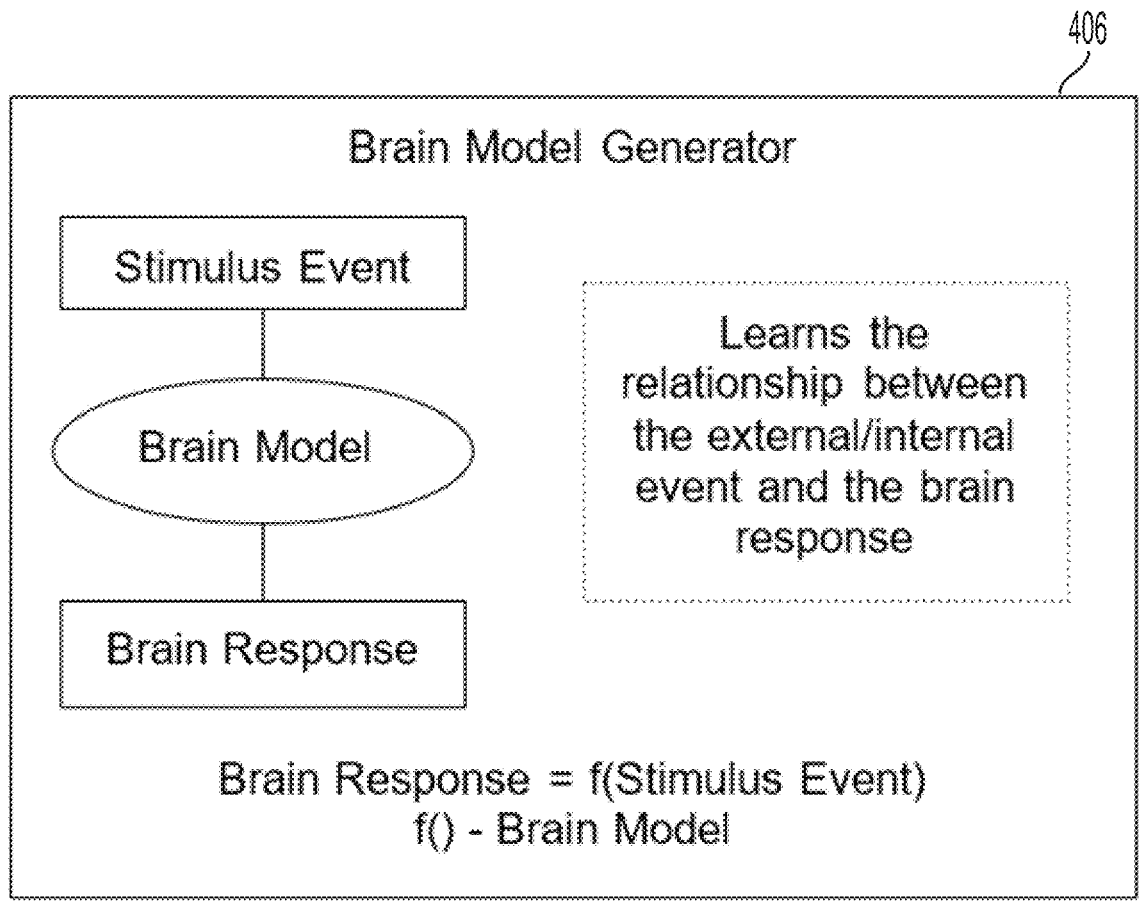
FIG. 13 illustrates a brain model generated to learn a relationship between an external/internal stimulus event and a brain response, according to an embodiment.

FIG. 13 illustrates the utilization of brain model generator 406 to generate a brain model that brain model learns the relationship between the external or internal stimulus event and the detected brain response by sensors 112.

Figure 6:
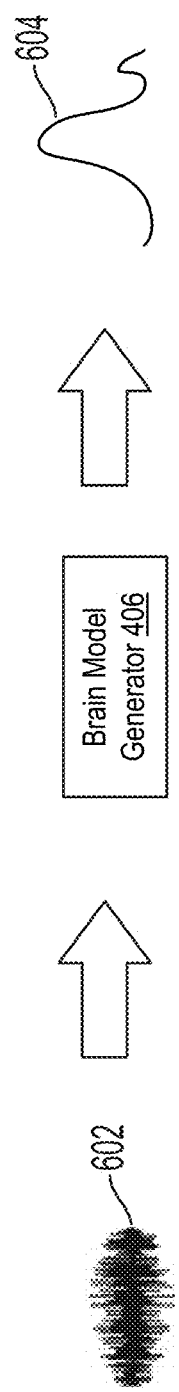
FIG. 6 is a schematic illustrating a conversion of bio-signal data to a brain model, according to an embodiment.

FIG. 6 is a schematic illustrating a conversion of bio-signal data to a brain model, according to an embodiment. In the embodiment illustrated, raw EEG signal data 602 is input to brain model generator 406, to generate a brain model 604.

A brain model may be generated from a user profile, in particular, including brain or bio-signal data, such as EEG data, obtained from a user. A user profile may contain brain data and other details about a user, such as demographics.

In some embodiments, a brain model may be generated by a combination of expert knowledge and machine learning. Given bio-signal/non-bio-signal data and feature event data, (1) the data may be curated and cleaned by experts using various preprocessing techniques such as filtering, normalization, artifact correction, etc. (2) Next, features are extracted from the data such that these features are a more precise representation of the input data. For example, features can be the spectral power of the brain signals in a specific frequency band. (3) Features are then used to train a machine learning model such as a logistic regression, random forest, gradient boosted trees or neural network, on a relevant task such as prediction of feature event data given bio-signal/non-bio-signal features. (4) Alternatively, a machine learning model such as a neural network can learn the optimal processing steps end-to-end to predict the brain model outcomes directly from raw bio-signal/non-bio-signal data.

Figure 11:
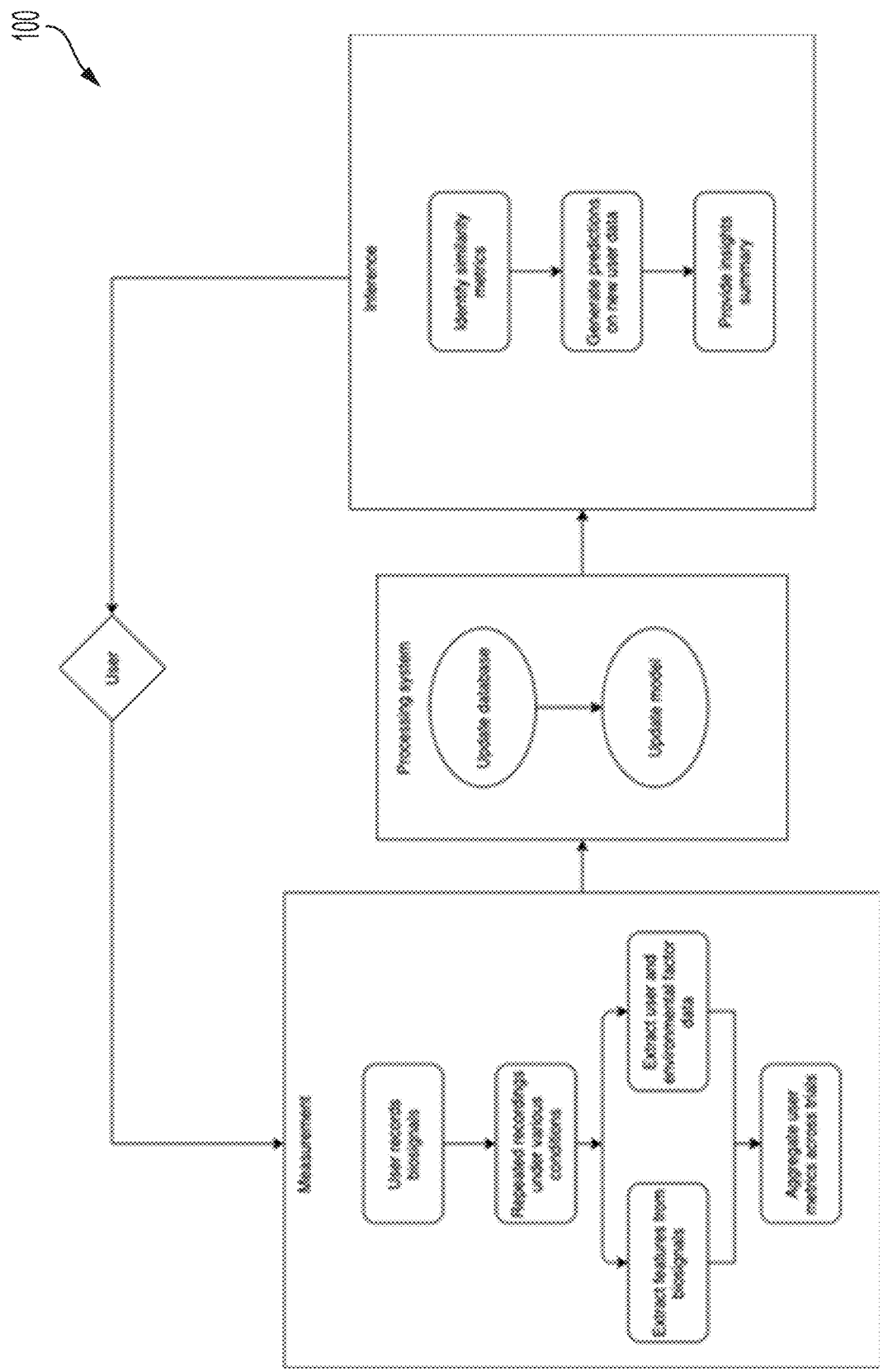
FIG. 11 illustrates a process to capture and process time-series bio-signal data, according to an embodiment.

FIG. 11 illustrates a process to capture multiple, simultaneous, time-series bio-signal data measured directly or indirectly from the human body across a population of users that can then be used to aggregate, identify, and differentiate within and between different users. A bio-signal model, such as that generated using the process of FIG. 11, may help users understand the effects of various personal, environmental, and chemical factors on their physiological responses.

Captured bio-signal data can includes (but is not limited to) electroencephalography (wet and dry), electrooculography, photoplethysmography, movement data using an accelerometer, thermometer, orientation data using a gyroscope, magnetic field intensities using a magnetometer, electromyography, galvanic skin response, kinematic data captured through an imaging modality using a monocular or binocular vision camera, facial recognition through a high definition digital camera in a handheld device, single purpose specialized camera or a personal computer, and a sound intensity sensor.

As illustrated in FIG. 11 at the "Measurement" block, bio-signals from a user, such as user 101, are recorded, such as wirelessly through a computing device such as local computing device 130 (handheld or otherwise). Such bio-signals are time-series data measured from some physiological processes in the human body. Depending on the nature of the bio-signal, certain deterministic characteristics occur under specific conditions that can be quantified and identified within and across different users.

In some embodiments, multiple recordings of bio-signals are taken under various conditions. Conditions can vary depending on a variety of factors including but not limited to age, gender, and geographical location.

Bio-signal data can be co-captured with several individual specific and environmental factors (also referred to as "labels" herein) including but not limited to time of day, food and chemical consumptions, medical conditions, emotional states, and sleepiness.

Co-captured bio-signal data and labels can be aggregated across multiple trials. The data can also be uploaded to the cloud database through an admissible route depending on network connectivity.

A processing system, illustrated in FIG. 11, can be responsible for storing, manipulating, retrieving and updating a cloud-based bio-signal model training protocol. The user database can be updated once the co-captured bio-signal data and labels are available on the cloud.

The processing system may implement a process to update the individual specific, personalized, aggregate bio-signal model. The base model used for modeling the bio-signal data and label feature space is based on but not limited to supervised, unsupervised, transfer, and semi-supervised learning methods.

An updated bio-signal model and its hyperparameters may be stored and used for deriving inferences for a user's new data, as illustrated in FIG. 11.

To generate predictions on a user's data that was uploaded to the cloud database, an inference generation procedure calculates similarity metrics based on the user and population data available in the cloud database.

The calculated similarity metrics, in addition to the raw, processed, and aggregated bio-signal features, are used as input to the personalized, aggregate bio-signal model.

Predictions generated by the bio-signal model can be used to provide auditory, visual, tactile, proprioceptive, thermal, and/or olfactory feedback depending on the experience and use-case for that particular session. Predictions are also used to provide the probability of a user belonging to a specific subset of population within each label using a visual display. A visual display can be made available through a mobile application in a handheld device, desktop personal computer, laptop, or any other web based interface.

The process illustrated in FIG. 11, forming an aggregate bio-signal model loop, can be used to provide to the user. Users can interpret and gain insights based on a single trial or across multiple trials longitudinally to influence their behavior. This information can also be made available to a subject matter expert upon user request to obtain volitional, professional feedback about their individual and/or longitudinal trials.

In some embodiments, feature extraction and classification of bio-signal data and other data, such as time-coded feature event data, by data processor 404 may be used to generate a brain model.

In some embodiments, a set of features extracted and classified from bio-signal data, such as brain data, may be collected, quantized and stored as a brain model.

In an example, brain data from users that are meditating can be preprocessed and transformed into relevant features such as power in given frequency bands and statistics of the different brain data channels. The distribution of the features can then be estimated, for instance by dividing the space of possible values into different bins, and mapped to feature event data or expert knowledge to act as a brain model. The parameters of the distribution learned can finally be stored.

While supervised learning methods are the most common and well understood methods in machine learning, they are limited by their heavy reliance on annotated data samples. Generally speaking, for a supervised learning model to perform well on any given task, it will require hundreds to millions of labelled examples, which can be costly, time consuming, or simply impossible to collect. In the case where few annotated data samples are available, unsupervised learning techniques can be used to learn a model that can either 1) be used as brain model directly, 2) be fine-tuned using the (few) annotated data samples that are available to obtain a more accurate or robust brain model (an idea similar to the idea of "transfer learning") or 3) used as a feature extractor to produce general data-driven features to be reused in other brain models.

In some embodiments, unsupervised learning models can be trained using self-supervised learning, a subset of unsupervised learning techniques, in which a model (such as a neural network) is trained on a pretext task that generates annotated examples using the structure of the data itself. For instance, predicting whether two 30-s windows of brain signals are close or far from each other is a self-supervised learning pretext task.

In some embodiments, unsupervised learning models can be trained on an auto-encoding task, in which a model is trained to reconstruct its input given constraints such as dimensionality reduction of the internal data representation, sparsity of the internal data representation, or de-noising of its input.

A brain model can also be trained by using cross-dataset training, where both user data and external data are used jointly to learn a better brain model (e.g., more accurate, more specialized, or more robust). In the machine learning literature, this would be seen as a form of "domain adaptation". External data can refer to any set of recordings obtained through another system than the currently described system. For instance, this could be an openly available dataset collected by a research group on a specific subset of the population (e.g. patients with suspected sleep apnea, patients with seizures, individuals with depressive symptoms, etc.) or following a well-defined protocol (brain-computer interfacing experiments, cognitive and affective monitoring tasks, etc.). The external data could also be privately owned datasets to which access has been granted.

Using both the user collected data and the external data, supervised and unsupervised learning brain models can be trained by optimizing a cost function defined on both data sources. For example, a neural network could be trained to predict occurrences of sleep apnea in an external dataset of sleep apnea patients while being simultaneously trained to perform dimensionality reduction on user data. In doing so, the brain model can leverage the specificities of the external data while keeping its ability to interpret user data.

A brain model, characterized in some embodiments as a "longitudinal" brain model, may be generated, for example, based at least in part on repeated measure data that is collected by data collector 402 and processed by data processor 404 which includes short interval metrics over repeated measures.

A "longitudinal" brain model can be defined as a brain model developed using data collected over more than one recording. In an example, a brain model of a user might be formed on the basis of data collected from several days or weeks of use of the system.

In some embodiments, repeated measures can be used in the process of generating a brain model in a number of different ways, including: 1) Repeated measures can be used to assess whether patterns seen in the user data are robust and occur generally for a user, or if they are outliers, in which case they might be ignored. 2) Repeated measures can be used to assess how certain patterns vary with time, for example, how brain data varies during different times of the day, across seasons, with a consistent meditation or exercise practice, with different levels of sleep quality, etc. 3) In the case of a predictive application, repeated measures of multiple users can be used jointly to train a brain model that predicts when a specific outcome will occur, such as when a new user might see an improvement in their sleep patterns or meditation practice.

In one application, brain model generator 406 use a series of measures (such as repeated measures) of a user's brainwave characteristics from brain signals collected on several days as a set of input parameters for a brain model or an application such as neurofeedback training. The brainwave characteristics in question might include relative contributions of different oscillations, relative amount of non-oscillatory characteristics, transient brain potentials evoked by external stimuli, or transient brain potentials evoked by internal factors such as heartbeats or body movements.

For a user a base brain model may be initialized based on the user's profile and classification parameters. As a user uses an application, collected features (such as features extracted and classified from bio-signal data) can be used to further populate the feature space, building on the base brain model and to allow for the optimization of their classification parameters.

Such a base brain model may be a neural network that is generated by transfer learning (from "like" or similar users) and then parameters of the neural network tailored via learning to a specific user. The model may then be optimized with new data, and that version of the neural network tuned for parameters for that individual, and that brain model for that user.

Transfer learning can be of two types: 1. Transfer learning in the context of subjects. Wherein data from similar users are pooled together to generate a brain model. 2. Transfer learning in the context of user-customization or fine-tuning of the Brain models. Wherein, a base model is adapted to a specific user's data.

Updates to a user's brain model can be applied both on a client device, such as client computing device 130, as well as on a server, such as remote computing device 140. Updates on the client side are typically done on-line to optimize real-time performance (e.g. to sustain or improve performance across a session).

Techniques described herein may allow for changes over time to brain to be tracked, for example, using repeated measures as described herein, as the brain is "plastic". As such, a brain model may be updated and revised based on machine learning and refinement as described herein.

Collected user data may be aggregated on a server, such as remote computing device 140, such that a more comprehensive learning process may be applied such that a user's base model can be updated to improve the fit of the model to the user. These full data methods are run on the server because of their complexity and to add value to data uploads for the user. It also allows for analytics to be performed, and in an example, provided back to user 101 through a web-portal.

Figure 12:
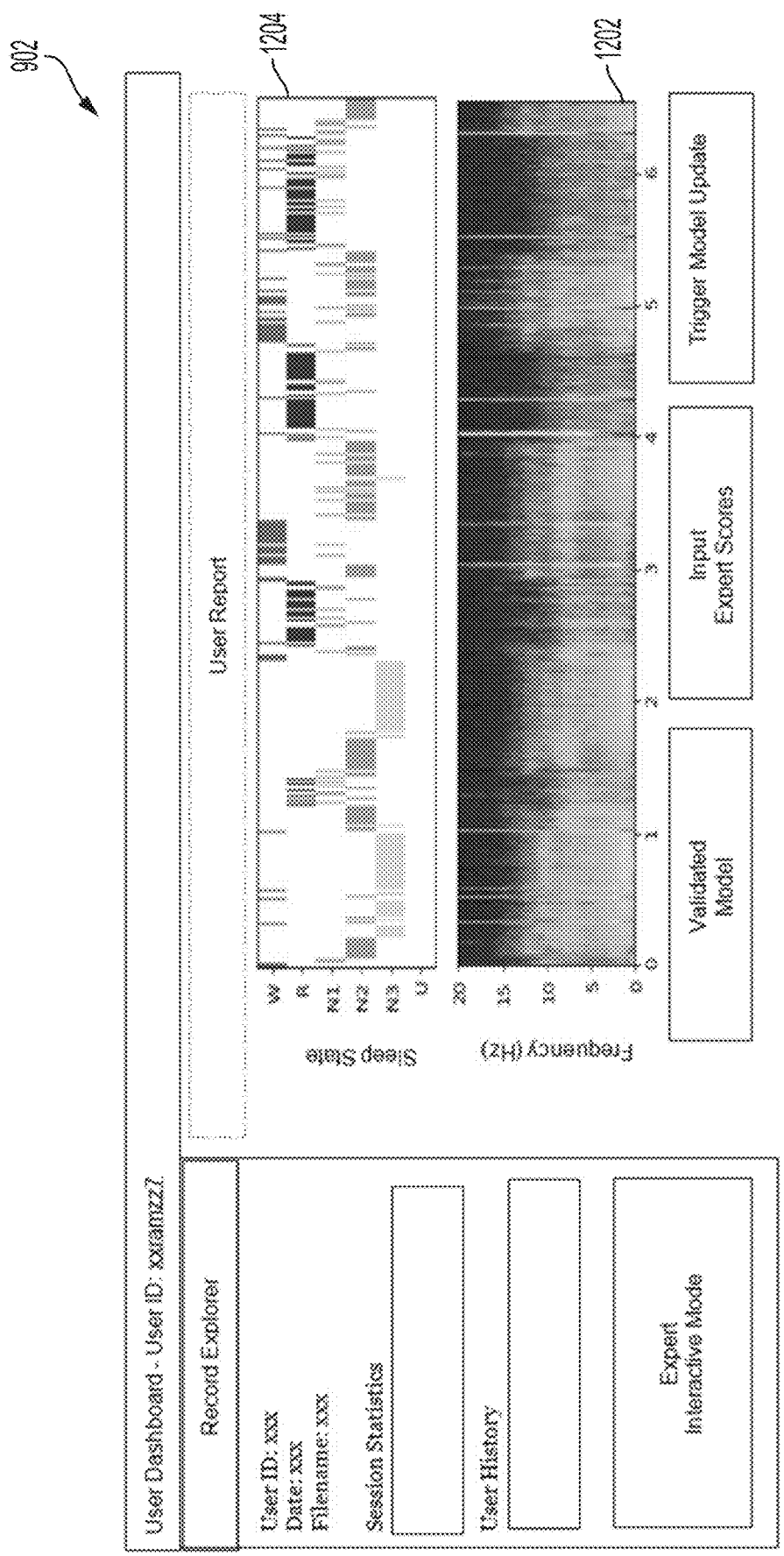
FIG. 12 is a screenshot of an expert view/dashboard, in accordance with an embodiment.

FIG. 12 is a screenshot of an expert view/dashboard 902, in accordance with an embodiment.

An expert-view/dashboard 902 can serve purposes including (1) Offline Algorithm Validation and Development (Validated Model, Input Expert Scores, Trigger Model Update), and (2) Online Improve/Modulate User experience in Real-time (Expert Interactive Mode).

In some embodiments, sleep state data 1204 is output from a brain model. A brain model may be a mapping from raw brainwave data 1402 represented in the frequency domain. The brain model may be used to map raw brainwave data 1402 to lower dimensional sleep states 1204 recognized in the field. From this, in an expert viewing mode, access may be granted to raw data and predictions. In some embodiments, there is an option of making annotations of files, like a manual override, which can indicate certain conditions are not as model suggests, but actually something else.

For Offline Algorithm Validation and Development, examples include comparing the current model's predictions, biological signals, and self-annotations by the expert.

For Online Improvement/Modulation to User Experience in Real-Time, to induce changes in a user's experience, real-time monitoring and tracking of biological data and brain states. For example, to play suitable music/story/trigger emotional states when one is in one or many sleep states, to wake the user in one or many sleep states.

Brain model performance validator 904 may be configured to perform validation of a brain model. Periodically, a brain model performance validation trigger can be used to verify the brain model's performance in the field. The validation can include a subject matter expert to look into specific user's single or multiple sessions and validate the current brain model's performance. As an example, the subject matter expert can validate the current user's sleep state prediction model by viewing their data along with the model's predictions. The expert view/dashboard 902 can also provide the expert to self annotate the user's data. If the base brain model's predictions and the expert annotations have high similarity, then fine-tuning/model update process is not triggered. Whereas if the similarity is lower than the expected threshold, then this will trigger a fine-tuning/model update process. The user-customizer process will be invoked. The fine-tuning can leverage methods such as transfer learning In some embodiments, a brain model may be user-specific, and associated with a particular user, or a user identifier.

In some embodiments, a brain model may be associated with multiple users.

A brain model can be expressed using various techniques or different types of models, including linear models (logistic regression, linear discriminant analysis, Gaussian naive Bayes classifier, linear support vector machines), nonlinear classifiers (nonlinear support vector machines, random forests, gradient boosted trees, k-nearest neighbours classifier), neural networks (fully connected neural networks, convolutional neural networks, recurrent neural networks, long short term memory neural networks, residual neural networks, autoencoders, restricted Boltzmann machines, generative adversarial networks, capsule networks, or a combination of all of the above), histogram, standard parametrized distribution (multivariate Gaussian, Wishart, etc.), expert system, or other suitable model.

In some embodiments, a brain model may be expressed as a linear model such as a linear regression model, a neural network, a histogram such as a multidimensional histogram.

A type of brain model may be selected as appropriate for its application. A specific technique might be chosen to implement a brain model for a given application such that it provides adequate expressive power while minimizing computational complexity. For example, in the case of a brain model whose purpose is to classify stages of sleep, a convolutional neural network might be the most appropriate choice of technique as it provides enough expressivity to detect variations in sleep data, while requiring relatively few parameters as compared to a fully connected neural network. For a brain model that is targeted at predicting complex pathology such as depression, a set of more complex techniques might be required, such as the combination of a convolutional neural network, recurrent neural network, handcrafted features and shallow classifier, as well as an expert system. On the other hand, a brain model with a simpler purpose such as detecting when the user has their eyes open or not might consist of a hardcoded decision rule applied to brain data features.

Figure 7:
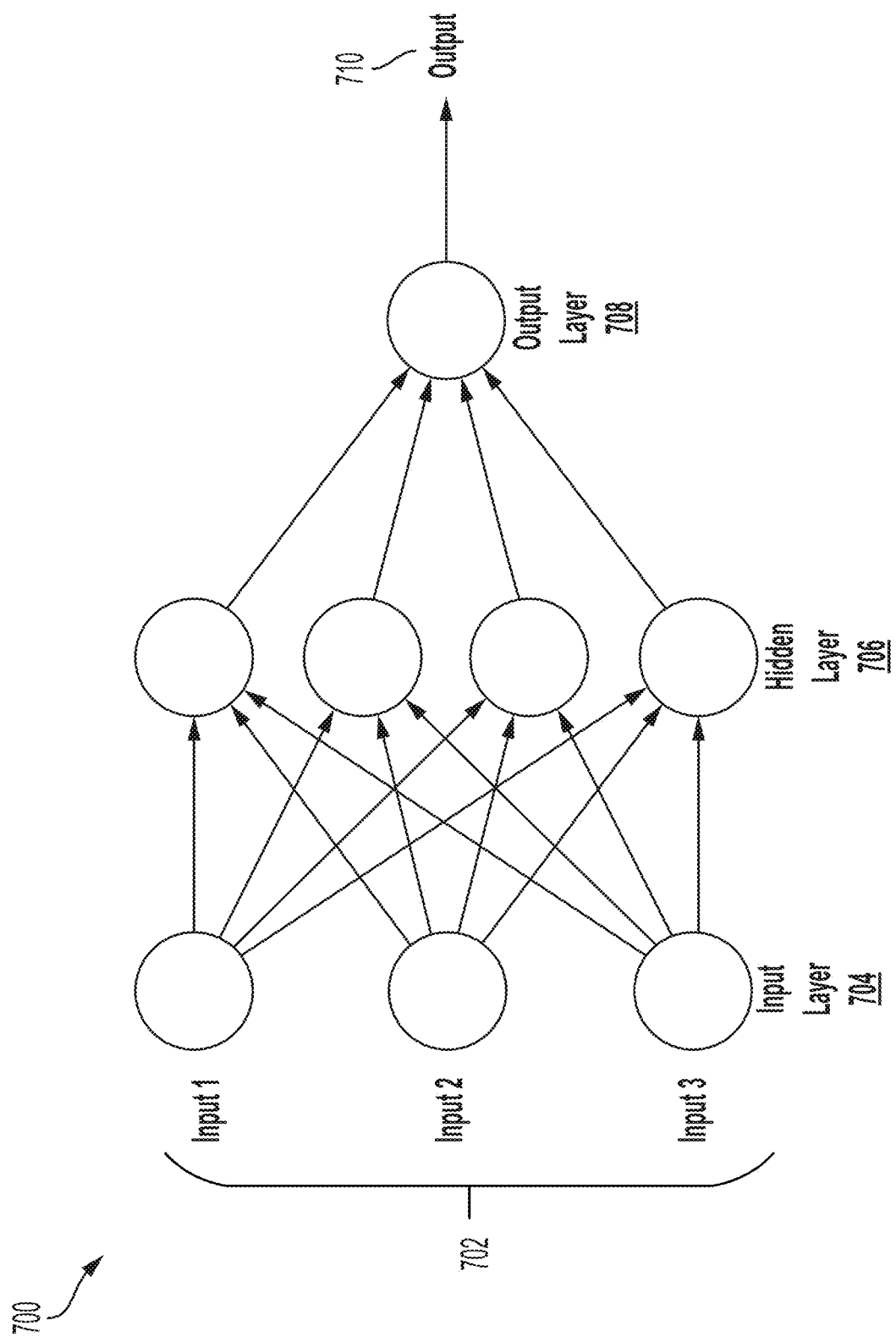
FIG. 7 is an example of a neural network architecture to express a brain model, according to an embodiment.

An example of a brain model expressed as a neural network 700 is illustrated in FIG. 7. Inputs 702 to neural network 700 can include bio-signal/non-bio-signal data input to an input layer 704, to one or more hidden layers 704, and output layer 708 to output 710.

A neural network can be defined as a hierarchical processing structure that processes input data in increasingly complex and abstract ways, and that can be trained on a set of data ("training data") to perform a given task with the goal of minimizing a cost function. Usually, a neural network is composed of a cascade of linear transformations followed by nonlinear functions which increase its expressive power. Each set of linear transformations is called a "layer", and each layer contains units or "neurons", which each receive and process (part of) the data coming from the previous layer. There exist variations of the standard vanilla neural network architecture, for example layers that perform convolution by applying "kernels" or "filters" that span local regions of the input or intermediate data (convolutional neural networks), or connections to previous processing time step(s) (recurrent neural networks).

A neural network can be trained on the collected bio-signal/non-bio-signal data such that it can perform a given task (for instance, predicting sleep stages from sleep brain data). In that case, the neural network itself, defined by its architecture and the values of its parameters ("weights") is the brain model.

A brain model may be stored in brain model store 490.

In some embodiments, a brain model may include parameters or features of a neural network trained for a specific user. Thus, the brain model may reflect a collection of data obtained about a user, and simplified into a smaller set of parameters, but may still carry salient information. Thus, a neural network may be trained to recognize and predict a user's brain data. Within the user's brain data is contained a lower dimensional representation of a user's brain data.

By training a neural network to understand a user's patterns, the weights of such a network contain information related to a user. It may thus be possible to generate a dimensionality reduced representation of user's brain, by taking totality of a user's brain information, and turn into lower dimension representation of the brain information.

A neural network may be trained and used as a base model (baseline or default), and by way of transfer learning, re-purposed for training a model for another user, as described further herein.

In terms of storage, it may be the case that given particular algorithm, the feature space for a brain model may be shrunk without damaging ability to optimize an algorithm, for e.g., by saving a user's brain data as representations of alpha brainwaves (for example, in the frequency range of 8-12 Hz) (or alpha "power") or theta brainwaves (for example, in the frequency range of 3 to 8 Hz) (or theta "power"), and aggregating those to store the rest of the data in cloud to reduce burden on transmission lines and processing on mobile device to make meaningful optimizations to how device is functioning. Decisions for reducing feature space may be made based on a desired application, providing ways of slimming down data for performance reasons.

In some embodiments, brain model generator 406 is configured to perform transfer learning for developing brain models of users. A group of users may have associated brain models with common features. Transfer learning can be used to transfer data relating to these brain models to develop another brain model for another user.

Transfer learning may be used to develop a base brain model for a user based on other brain models for users with similar attributes or features. A base brain model that is closer to the user than a generic model can be used as a starting point for developing a brain model for that user or other users.

To identify users with similar brain models, a map of users may be created, to identify other users that "look" like a particular user having similar attributes or features (for example, similar power spectrum and variances in power spectrum when engaging in some kind of activity). In this way, it may be possible to reduce the universe of models to find a similar model.

Transfer learning may be applied to users that are "similar". In some embodiments, users may be determined as "similar" by comparing brain models associated with users. Users may also be identified as having "similar" brain models by comparing relevant characteristics for users and characteristics that have covariance and/or correlation may indicate "similar" brain models. By way of example, such relevant characteristics may include one or more of power spectrum, phased synchronicity, fractal dimensionality, non-oscillatory characteristics from EEG, and non-stationary characteristics.

Conveniently, transfer learning may be used as a way to localize a brain model from a smaller set of brain models based on similar attributes of users. This enables brain model generator 406 to shrink down the universe of possible brain models to a subset based on common attributes or environmental factors. In this way, processing may be more efficient based on a smaller universe of users. For example, in a neural network, this may be accomplished by freezing a state of different nodes in a network, and look at the shrink in activity based upon that.

In some embodiments, a model can be a neural network with a set of parameters—that model can be efficiently determined using transfer learning from similar users—then the model can be updated for a particular user by tuning or updating the parameters.

In an example of user model generation and customization, FIG. 14 illustrates a sleep state prediction model 1400 based on convolutional neural networks (CNNs), generated using systems and methods disclosed herein. The architecture consists of an Input layer, several convolutional layers, flatten layers, concatenation layers, fully connected layers and a softmax prediction layer. For example, multi-channel or single channel EEG data in the time domain or a transform domain representation can be provided as input to the CNN. This can include a windowed time series or a frequency domain transformed time series.

The model illustrated in FIG. 14 can contain several convolutional layers and can also contain one or several branches of convolutional layers. In the convolutional layer a kernel/filter operates on one or many dimensions of the input signal. Each convolutional branch contains different kernel/filter sizes that extract certain EEG patterns, EEG channel combinations and EEG frequency characteristics. Subsequent convolutional layers perform additional filtering that will enhance the features to provide a good class separation. In FIG. 14, a 'Conv' can include one or all of the following layers such as normalization/batchnormalization, activation function, pooling (max/min/mean pooling), dropout regularization, etc. Finally, the features from one or multiple convolutional branches are concatenated into a single feature vector or embedding. Based on this, the fully connected layer classifies a given input into one of the different brain states/sleep states.

The brain model illustrated in FIG. 14 can also include additional layers such as a linear model or a sequential model that predicts the sleep states based on the learned feature embeddings provided by the CNNs.

In some embodiments, a brain model may be a histogram such as a multidimensional histogram, in an example, with time as one dimension.

A brain model implemented as a multidimensional histogram can be generated by binning the features extracted from bio-signal data according to multiple dimensions, for example amplitude, time, bio-signal modalities and channels, etc. Regions of the multidimensional histogram can then be mapped or linked to specific decisions or predictions, such as whether a subject is focused or not. In the case of repeated measures, the multidimensional histogram can 1) be updated in such a way that it is more robust to recording-specific noise or outliers, or 2) include longer timescales as an additional dimension of the histogram, for example days or weeks.

A covariance matrix of features is an example embodiment of a brain model. A brain model expressed as a covariance matrix of features can encode the relationship between different features for a set of conditions. In this sense, a covariance matrix can be seen as a summary statistic of the distribution of features under a zero-mean multivariate Gaussian distribution prior. For example, the covariance matrix can encode the strength with which different input data streams or features such as power in different frequency ranges vary when other dimensions are varying. A high absolute value indicates that two dimensions (such as the power in a low frequency band and the power in a high frequency band) are strongly linked, whereas a value close to zero indicates that there is limited to no link between the two dimensions.

An example of a brain model is to take parameters from an individual (such as bio-signal data received from a sensor 112), an individual's environment (such as non-bio-signal data received from a sensor 112 or other suitable source), and other users in the user's vicinity and build a covariance matrix as determinative input to a brain model.

In some embodiments, a covariance matrix is built by computing the variance of each dimension of the set of features, as well as the covariance between each dimension of the set of features and the other dimensions. When only few samples are available, regularization techniques can be used to improve the estimation of the covariance matrix.

In an example, a brain model is the feature axes of the histogram, or in the case of a covariance matrix brain signatures, the brain model would be the set of features that the client pipeline estimates.

Typically the brain model used at a client computing device 130 is a covariance matrix of the subset of features that are most salient, given the computational resources of client computing device 130 that are available for feature extraction and classification.

In one embodiment, brain model generator 406 may add a forgetting factor to the histogram accumulation process to allow for adaptation to the covariant shift that is experienced in the variables as the user learns. In most cases brain model generator 406 does not forget the histogram initialization, in order to stabilize the adaptation.

In another embodiment, all of the data that has been transformed into the histogram space, are stored individually as a multidimensional time series, and the covariant shift of these features are estimated using a model predication, such as a low-dimensional polynomial model.

Brain model generator 406 may also be configured to generate a brain signature. A brain signature can be a unique identifier, specific to each user, that is derived from their brain model. The brain signature can be extracted from the brain model by reducing the dimensionality of its output(s), or by hashing the parameters of the model.

In an example, a brain signature may be an instance of a brain model for that user. A brain signature may be an extraction of unique identifier from biodata, the biodata stored for example in a brain model. In an example, a brain signature may be a reduced dimension version of the brain model.

In some embodiments, a brain signature may be a dimensionality reduced version of a user's profile data or brain model.

A brain signature may be stored in brain model store 490.

Brain model generator 406 may also be configured to determine a brain age, for example, of user 101.

Brain age can be defined as the age that is predicted by a statistical model trained on a healthy population, given a user's brain data. If the difference between the predicted brain age and the biological (or chronological) age of a user is significantly positive, then the user's brain effectively "looks" older, which might be caused by pathology or accelerated aging.

In an example, a "brain age", which may be different from "life" age, is a reduced dimensionality version of a brain model, which may be a parameter/feature of interest. Brain age can be used in specific applications or other brain models as an index that characterizes the health of a user.

A brain age may be stored in brain model store 490.

User customizer 408 may be configured to customize aspects of system 100, or particular algorithms, based on a user's brain model and profile.

Each person's brainwaves are different, therefore requiring slightly different tunings for each user. Each person's brain may also learn over time, and systems and methods disclosed herein may change algorithm parameters over time in order to adapt processing to the person's brainwaves. New parameters may be calculated based on collected data, and may form part of a user's dynamic profile (which may be called bio-signal interaction profile). This profile may be stored in the cloud, allowing each user to maintain a single profile across multiple computing devices. Other features of the same or another non-limiting exemplary implementation may include: improving processes through machine learning applied to collected data either on-board the client device or on the server; saving EEG data along with application state to allow a machine learning algorithm to optimize the methods that transform the user's brainwaves into usable control signals; sharing brainwave data with other applications on mobile device through a cloud services web interface; sharing brainwave data with other applications running on client devices or other devices in the trusted network to provide for the user's brainwave data to control or effect other devices; integration of data from other devices and synchronization of events with brainwave data aid in context aware analysis as well as storage and future analysis; performing time locked stimulation and analysis to support stimulus entrainment event-related potential ("ERP") analysis; and data prioritization that maximizes the amount of useful information obtainable from an incomplete data download (i.e. data is transmitted in order of information salience).

The profile of a user may also include one or more preferences of the particular user for embellishing their content. Each person's brainwaves are different, therefore requiring slightly different tunings for each user. Also, people learn to control their brain-state over time, and therefore parameters relevant for creating or updating the brain-state profile may change over time. New parameters can be calculated based on collected data, and can form part of a user's dynamic profile, by operation of the profile manager.

A brain model and a user profile can be used in conjunction with a set of algorithm pipeline parameters to classify a user's state (user response classification).

In some embodiments, a brain model may be used to predict a user's brain state on the basis of previous brain state.

A brain model can associate specific patterns in bio-signal data of a user to a set of descriptive dimensions (e.g., description of a user's cognitive or affective state) by means of statistical modelling techniques or machine learning techniques. Given the input bio-signal data, the brain model can use the prior information encoded in its parameters (e.g., the weights of a neural network) to process and extract relevant information and produce a prediction.

Prediction of expected brain performance/score/metric may be performed by systems and methods described herein, and based on, for example, calendar events, life events, recent activities, patterns of activity e.g. exercise/sleep, time zone change/seasonal change/latitude change, weather/local environment/luminance. In one example, a brain performance metric is reaction time.

In some embodiments, brain performance is a measured brain value relative to an established baseline for an individual.

In a broad sense, brain performance may be a brain state that has been identified as preferable, and evaluating someone against that.

In some embodiments, brain performance may be an analysis of brain responses that are outside of an expected response, for example, as identified in a brain model.

A specific example of "brain performance" might be a brain state associated, for a given user, with improved retention of information (as measured by later recall) or a state associated with higher rate of correct responses in a challenging task, or with a faster response rate—or the converse in each case. Other inputs to the model might include the amount of sunlight exposure the user has received in the previous day or week, or a user's amount of physical activity, as (for example) increased exposure to sunlight can be related to a user's mood and motivation, and certain amounts of rigorous physical activity can be associated with changes in performance on certain cognitive tasks.

For example, prediction of brain performance based on calendar events could be based on when a user wakes up, and what a user is doing at a particular time.

In another example, brain signals plus environment, may be used to improve or revise a brain model.

In some embodiments, data may be integrated from many sources, and systems and methods described herein may have connectivity to many other sources of information. These sources may provide data to further enhance and improve brain models.

Environmental predictor 412 may be configured to detect the environment by different means, such as those described below (e.g., actimetry, video capture, user feedback, etc.), and then use environmental measures as external markers that can be used as covariates when developing or using a brain model. Then, using a specific brain model, activity or environment of a user may be identified, and the brain model adapted, for example by ignoring movement artifacts in the case of an activity that involves movement, or reducing the frequency of audio or visual feedback if the user is working.

Environmental measures may be measured during the capture of brain data, to be used to determine an environmental state of a user. Examples of environmental states include sleeping, working, meditating, sports activities such as driving a golf club, or any other physical or mental activity of life, and so on. In some embodiments, determining an environmental state can be correlated with a brain model, which can be used to make predictions about a user's environment.

Environmental state can be determined by different means. For example, actimetry can be used to identify the types of movement executed by the user (e.g., walking, running, yoga, etc.). User feedback can also be used to identify the environmental state by directly asking the user to provide information as to what activity they are performing. Similarly, the user might be asked to perform a specific activity to allow the model to learn what their data looks like in that context. Other types of sensors, such as cameras, microphones and proximity sensors can also be used to identify environmental context and activity.

Once the environmental states are identified, such as through any of the techniques described above, the brain model can adapt its predictions, for example by ignoring movement artifacts in the case of an activity that involves movement, or reducing the frequency of audio or visual feedback if the user is working.

In some embodiments, local environmental predictors of brain models/brain scores may be used to accelerate transfer learning and baselining/improve user experience based on other users in vicinity. For example, brain models that were designed for the same specific task can be identified, and therefore be reused in a transfer learning scenario.

In some embodiments, environmental predictors may be stored along with brain data as part of a user profile or a brain model.

Environmental predictors may be used as parameters for a brain model, to identify, for example, what a brain looks like in a particular environmental situation, as compared to other environmental situations.

In some embodiments, in creating brain model, environmental predictors may be used to either select a model or environmental measures may be used to separate data to create multiple models based on a variety of activities, to example, one model for being awake, and other model for being asleep.

As such, with the environmental predictors, multiple brain models may be generated for a person—while the user is sleeping, while awake, while driving a golf club, etc.

In an example, environmental predictors may be used predict and classify data so that it is applied appropriately. For example, if a user is sleeping, other models may be selected that were also based on sleeping. Those models may also be used to apply transfer models for sleeping to generic sleeping model for that user.

FIGS. 15-18 illustrate various applications for using a brain model to modify or control a user environment, which can be performed by system 100, according to embodiments.

Figure 15:
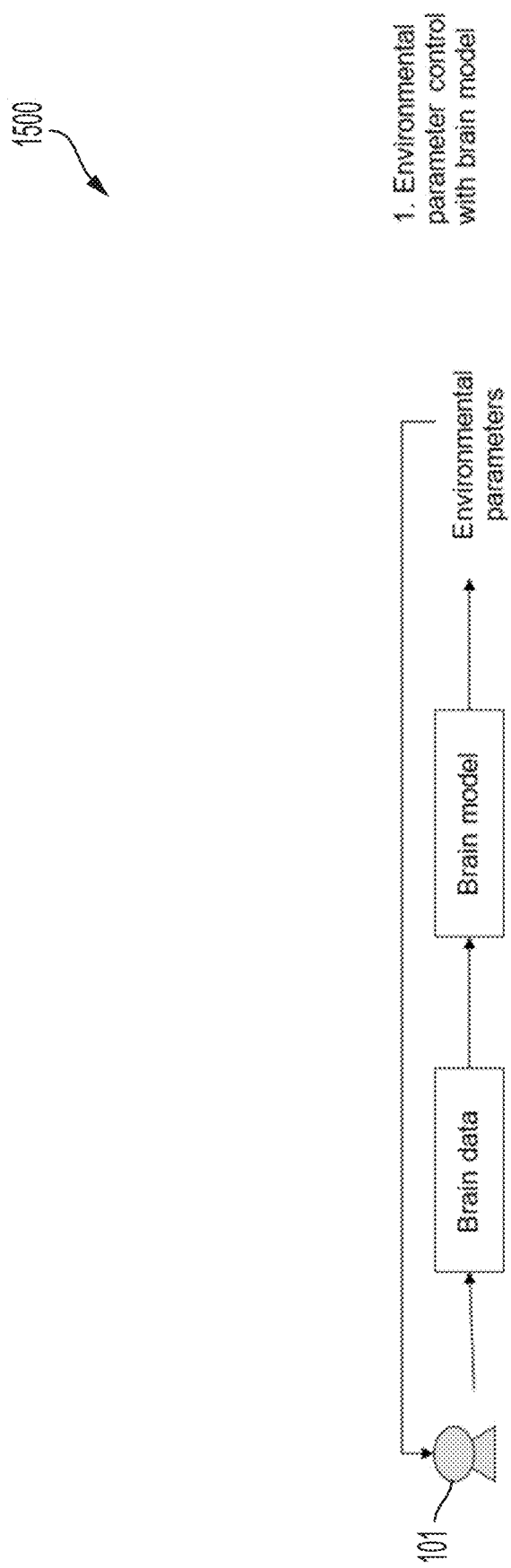
FIGS. 15-18 illustrate various applications for using a brain model to modify or control a user environment, according to embodiments.

FIG. 15 illustrates a workflow 1500 for a brain model used as a way to control the environment of the user while their bio-signals are being recorded. For example, the brain model can be used to play sounds or audio clips to help the user meditate, relax or fall asleep. More specifically, the brain model can be designed for particular types of environmental control.

Figure 16:
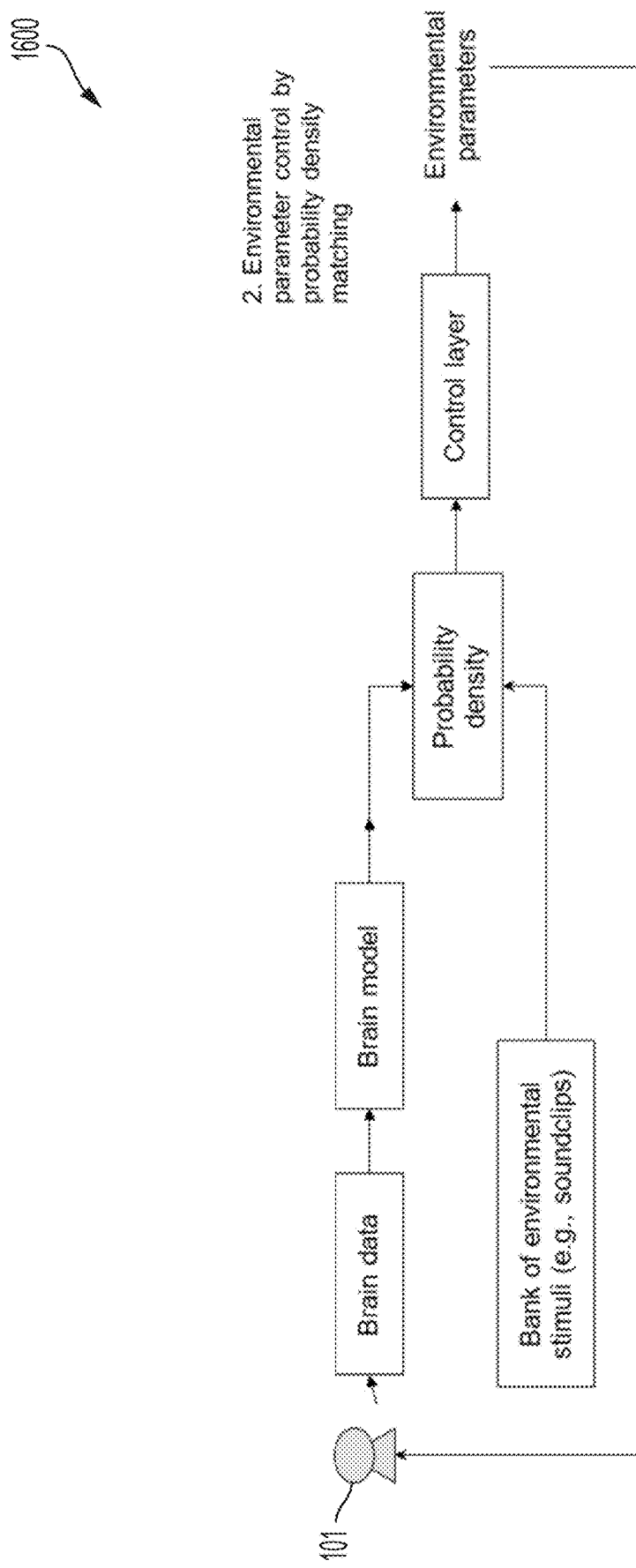

FIG. 16 illustrates a workflow 1600 in an embodiment in which the probability distribution over the outputs of a brain model can be transformed into a known probability distribution (for example a standard multivariate Gaussian distribution or a more complex distribution parameterized by a neural network). This known probability distribution is defined such that it matches the distribution of particular parameters of the environment of the user, such as background sounds, audio clips, music, lights, images, etc. For example, this second probability distribution could be a distribution over a bank of recorded sounds. In this scenario, the neurophysiological activity of the user will be translated into sound which the user can experience in real time.

Figure 17:
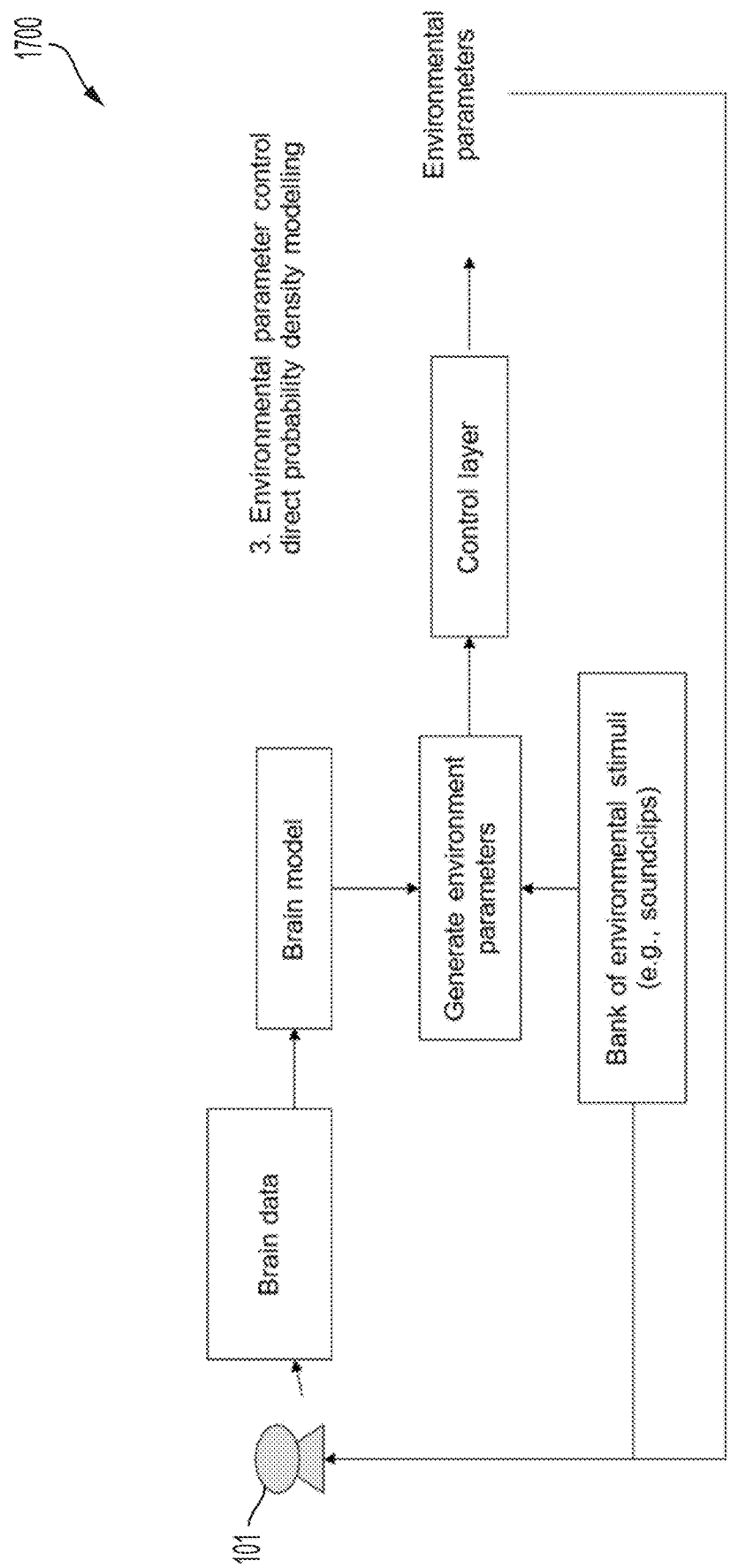

FIG. 17 illustrates a workflow 1700 in an embodiment in which a brain model can be trained to directly generate dimensions of the environment of the user. For example, given bio-signal recordings of a user listening to various types of sounds or music, the brain model could be trained to recover the sounds or music based on the recorded brain activity. Given new unseen bio-signal data, the brain model is then able to generate sounds or music that statistically correspond to the current brain activity of the user. Therefore, under similar neurophysiological circumstances, the environment of the user should be similar as well.

Figure 18:
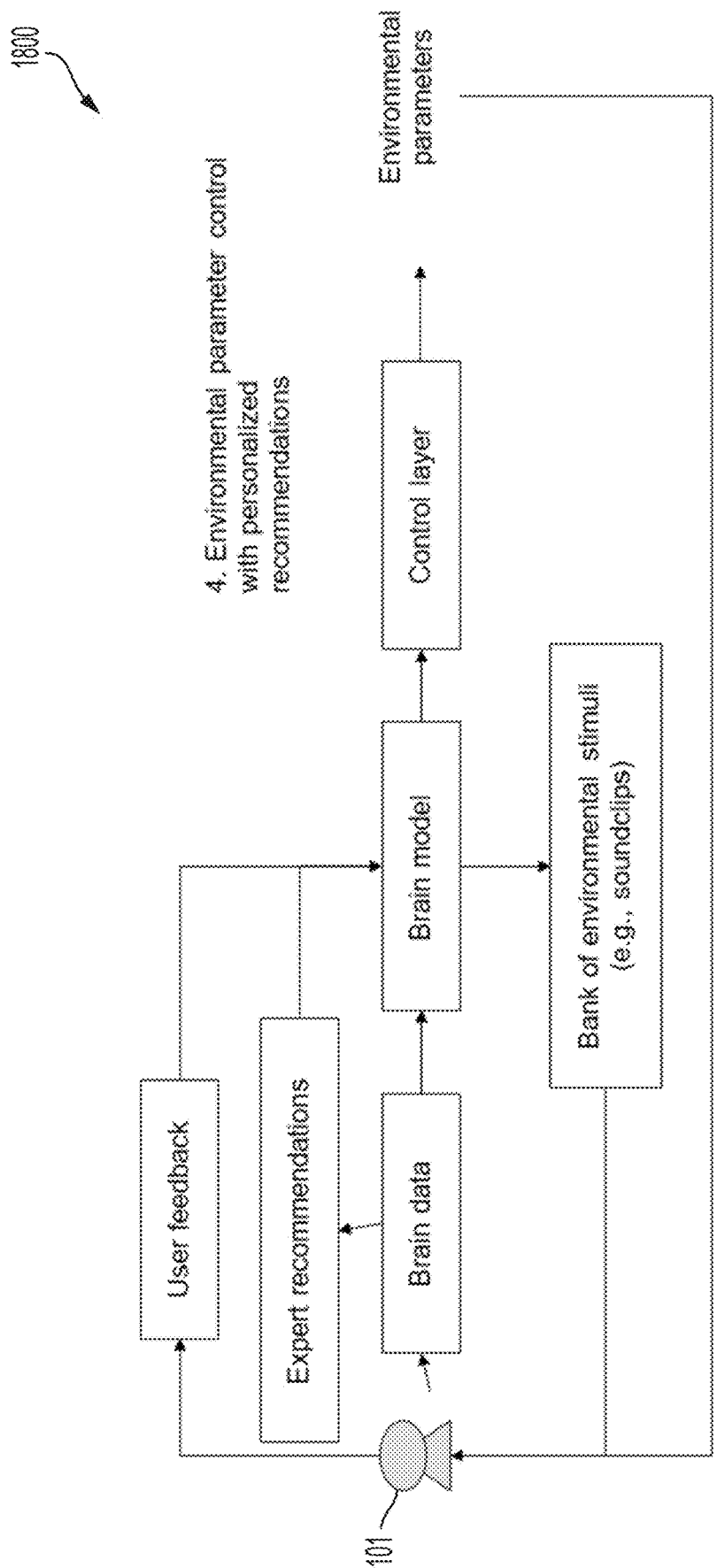

FIG. 18 illustrates a workflow 1800 in an embodiments in which a brain model can combine physiological insights and user or expert feedback to recommend soundscapes or music to the user based on their current mood or cognitive status. A system can identify types of sounds or music that impacts the user positively, such as feeling more relaxed or energized, and generate these kinds of sounds or music based on the current physiological activity of the user. The user can provide feedback as to which sounds or music help them feel better, or can flag sounds or music that are detrimental to their affective or cognitive status. Moreover, an external expert or observer can help identify these types of external stimuli that are helpful, which can be used by the recommender system to improve its recommendations.

Other applications of a brain model include for brain diagnostics. A user can wear a wearable, such as a headband, a number of instances (such as 5-10 times) to get a report about the probability of various neural conditions such as anxiety, PTSD, depression, Parkinson's, Alzheimer's, and the like.

A brain model as disclosed herein may be used for security, by providing personalized metrics from brain and cardiac signatures to unlock certain devices or access.

Evoked brain responses for speech, visual, proprioceptive and other non-stochastic, structured stimuli may provide an understanding of what users subconsciously respond to, for the benefit of health and well-being.

Augmented analytics may be used to correlate language and vision models to brain responses to understand the effect of speech/language latent features (such as inflections, sentiments, clauses, and phrases) and vision latent features (such as brand recognition, alertness to road signs, and response to mandatory training).

Brain model-based interventions can include optimization of non-invasive brain stimulation (electrical, tactile, optical) using personalized bio-signal models, and closing the loop on TDCS/TACS. These techniques may utilize impedance matching for recording and stimulation, and artifact rejection/suppression for cleaning EEG during stimulation.

Other interventions include optimizing prescription drug reps/dosage based on a brain model to account for default mode network and functional connectivity changes, for example, due to sedatives or antidepressants.

Attention brain models may be used to improve neuroplasticity during rehabilitation. For example, for a stroke, attention is a big factor in constraint induced-movement therapy. For autism/Asperger's/ADHD, training modules may be optimized based on personalized brain and bio-signal models.

For concussion or traumatic brain injury (TBI), a brain model may be utilized for objective measures of attention levels during standard tasks and daily activities of living.

During a fitness test, a stimulus can be part of the therapy.

In an example of PTSD treatment by way of exposure therapy, a user may be exposed to stressors, their response evaluated, and the intensity and frequencies of the stressors thus modulated. Monitoring and tracking, for example, as compared to a baseline brain model, may be utilized to determine if a user is improving. A user's response to a stimulus can be evaluated within safe bounds, or within a danger zone.

As a model is learned over time, a brain response to a novel stimulus can be predicted. Therefore, by learning different representations or brain models for different neurological disorders or conditions, responses can be simulated.

An additional therapeutic or medical parameter can be added as an input to a brain model, and the brain model may indicate how a response may vary for a particular user.

A user of the system might activate a brain sensing device connected to a computer, and instead of a starting with uniform parameters similar to all other users, the system might quickly compare brain characteristics of the user to that user's previous known brain characteristics to rapidly change the manner in which the computer responds to the user's inputs. For example: the brain model is used as a comparator to determine that a user's present brainwave characteristics indicate a high level of fatigue or impairment, or instead, a high level of focused attention, and alter the manner in which the computer presents information to the user—for example, to decrease the likelihood of user error with a computer.

A brain model and techniques disclosed herein may affords several useful applications that extend from the understanding into an individual's brain data and brain state it affords, and in particular, in relation to specific events, conditions, situations, environments, and/or experiences.

A brain model can, for example, be leveraged toward the identification (or determination) of progression paths through which continuation, alteration, deviation or cessation of a given event, condition, situation, environment and or/experience can be imposed.

Identifying a progression path can provide a means of establishing a personalized brain model within and among a variety of population-specific criteria yield to opportunities to gain insights into the relational reactivity of individual brain responses.

A potential use case of this progression path identification (or determination) would be in a setting of a caregiver or therapist administering a intervention to a patient through which the adjustment, titration, modulation, or variation of the intervention would occur in response to specific outputs from the patient's brain model as accessed by the caregiver, both in real time, and over a longitudinal progression of time through the further addition of inputs to the model.

In the case of psychedelic therapy, for example, the regulation of set, setting, and intensification of experience could be modulated and adjusted by a caregiver receiving outputs from the patient undergoing therapy in real time through which the patient's experience is modeled predictively in order to understand how their experience and temporal state could be anticipated to alter or vary throughout the course of treatment, in relation to their particular interaction and integration with the therapy. In order to optimize the efficacy of a psychedelic treatment, it is especially important to identify and determine the way in which a patient will experience its corresponding effects, such that success of treatment will vary depending on the specific and particular level of receptivity and comfortability with the therapeutic experience.

As a caregiver receives and observes the outputs from a patient's brain model, they are able to alter and vary the patient's therapeutic inputs, such as various sensory inputs, dosing inputs, duration of therapeutic setting, frequency and intensity of interaction, etc., in order to identify and safeguard against any untoward or negative response to treatment at an early enough stage such that course correction is readily possible, and treatment outcome is readily salvageable.

In one application, results learned in studies can be used to update a user's profile and brain model. For example, a user's profile may be updated to state that, based on the user's brainwaves and other information the user is at a higher risk for developing a particular disease or condition, which may be correlated to particular features of a brain model.

A brain model, as disclosed herein, can be incorporated in a treatment model for a user. In an example, a treatment model can generate a treatment or recommendation, on the basis of inputs, for example, in the form of a brain model, and an associated protocol.

In some embodiments, a brain model response to treatment can be classified, which may further be used as a technique for diagnosing.

System 100 may support conducting medical, anthropological or social studies with the data collected by system 100. System 100 may be used for the design a study protocol and select study parameters.

A study protocol and its parameters can include the definition of the population to be studied (e.g. ADHD diagnosis compared to normal), and the type of study to be conducted (e.g. randomized clinical trial (RCT), prospective or retrospective longitudinal cohort studies, cross sectional studies, pilot studies or other observational or clinical type of studies). A software based controller in system 100 can then execute operations for querying and selecting users, in a randomized fashion to belong to different study arms (e.g., sham versus neurofeedback). If the study is prospective or a comparison type study (e.g. RCT of different algorithms or treatment effects) then instructions may be given to users specific to each arm of the study for them to follow. The controller can then provide alerts to users to ensure that they are complying with the study protocol. Then the controller can gather the data relevant to the study, anonymize any identifiers and build a data set that can be analyzed offline by a human analyst or automatically online by study software built-in system 100.

System 100 may be designed to serve as an external and internal research tool. For internal research system 100 can serve as a driver for A/B testing with subsets of the user population for algorithm or application or user experience experiments. This testing infrastructure may also be useful for external clients or researchers looking to run targeted experiments on specific cohorts within the general population, such as a focused attention test for ADHD patients in a given age range vs. a similarly aged control group.

In some embodiments, a brain model as disclosed herein can be used to generate interactive embedded brain model state-based biofeedback, and conveniently may help users achieve desired brain states and avoid undesirable brain states.

In some embodiments, a brain model may predict a user's brain state in real-time. In the context of a meditation experience, this could include states such as: neutral, distracted, focused, compassion, and transcendence. In the context of a sleep experience, this could include various sleep states including light, deep, and rapid eye movement (REM) states.

Figure 19:
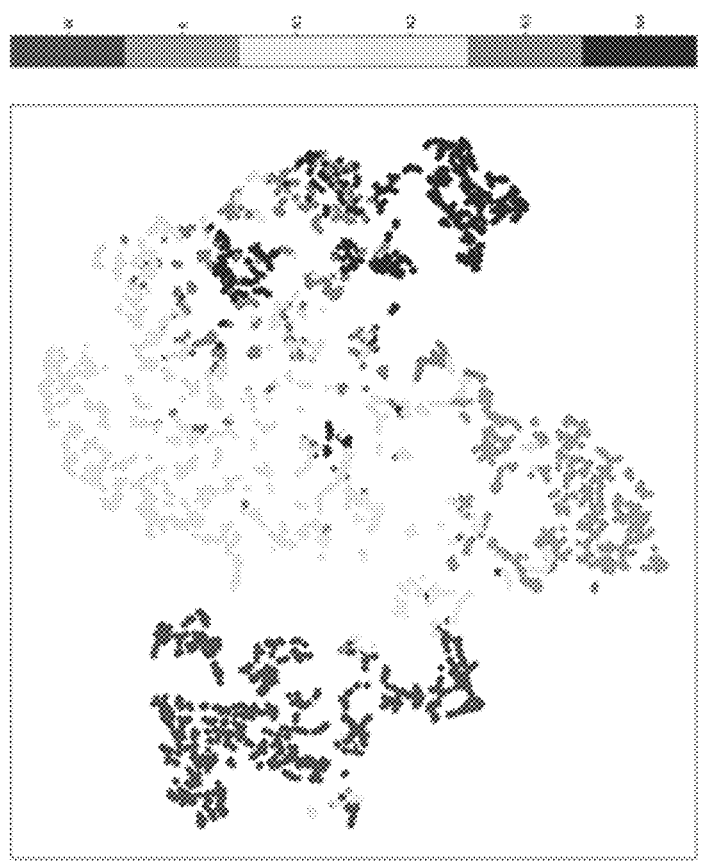
FIG. 19 illustrates an example below for a two dimensional embedded sleep state space encoded by a brain model, according to an embodiment.

In exploring the brain model's state space, a user is presented with a visual representation of the space of possible brain states, derived from the brain model's state space. As an example, a neural network-based brain model may be presented with a two dimensional latent representation, referred to as the embedded state space, though the dimensionality of the embedded space may be higher than two. The example two dimensional state space is presented visually, with different states differentiated by colour. FIG. 19 illustrates an example below for a two dimensional embedded sleep state space encoded by a brain model. Distinct brain states are encoded as distinct clusters, e.g. W: Wake, R: REM, while brain states that share a continuum are encoded with smooth transitions, i.e. non-REM sleep states N1-N4. FIG. 19 thus illustrates a flattened brain model, mapped from higher dimensions to a two-dimensional representation.

Figure 20:
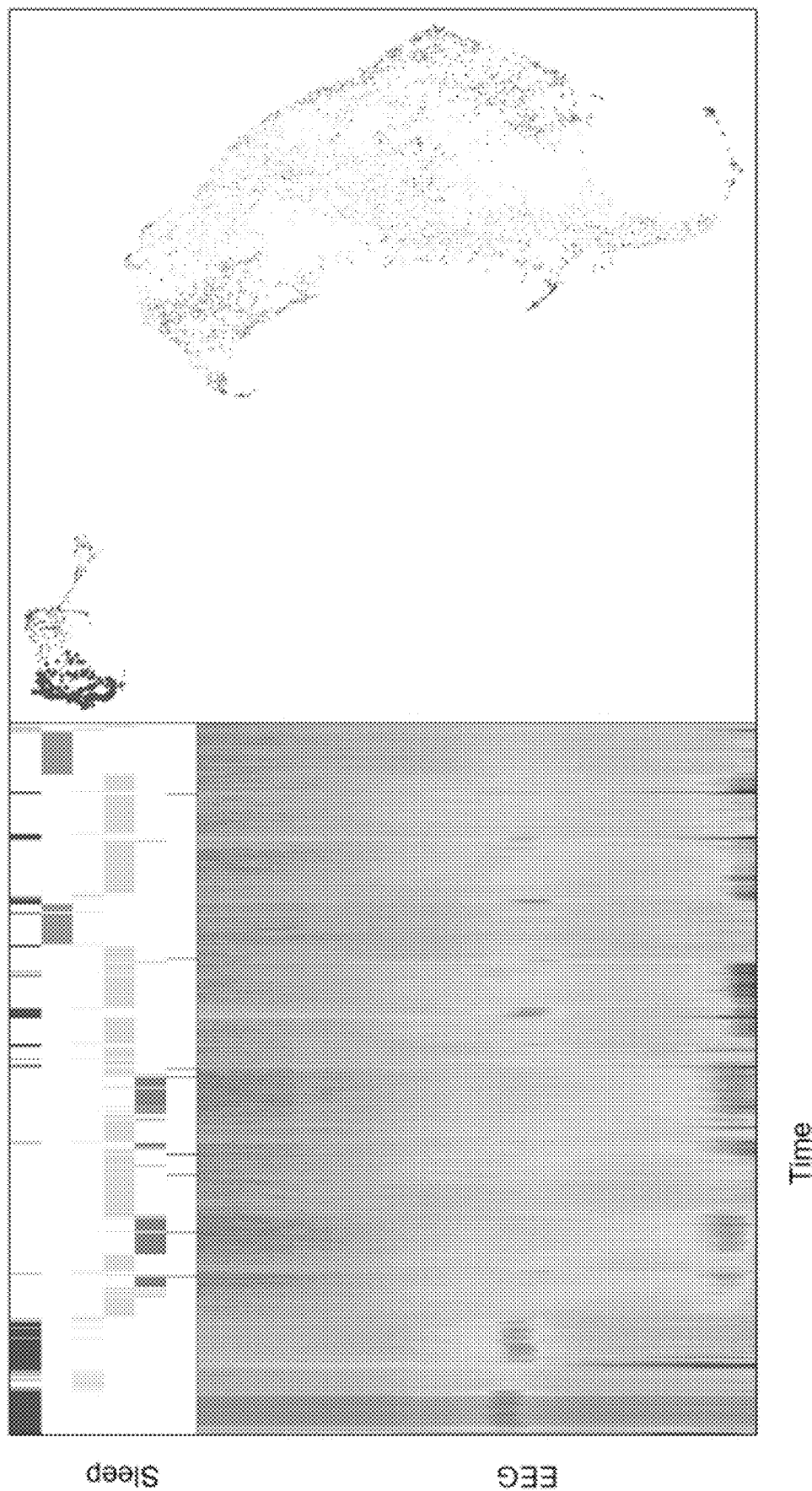
FIG. 20 illustrates a visual representation of the time course of brain data presented alongside a brain space model, according to an embodiment.

FIG. 20 further illustrates a visual representation of the time course of brain data presented alongside the brain space model. This can allows a user to both determine their brain state visually in real-time, as well as to revisit a recorded session and interactively determine when they were in which state. The user may select regions in time, with the corresponding points then highlighted in the brain model state space representation.

Figure 21:
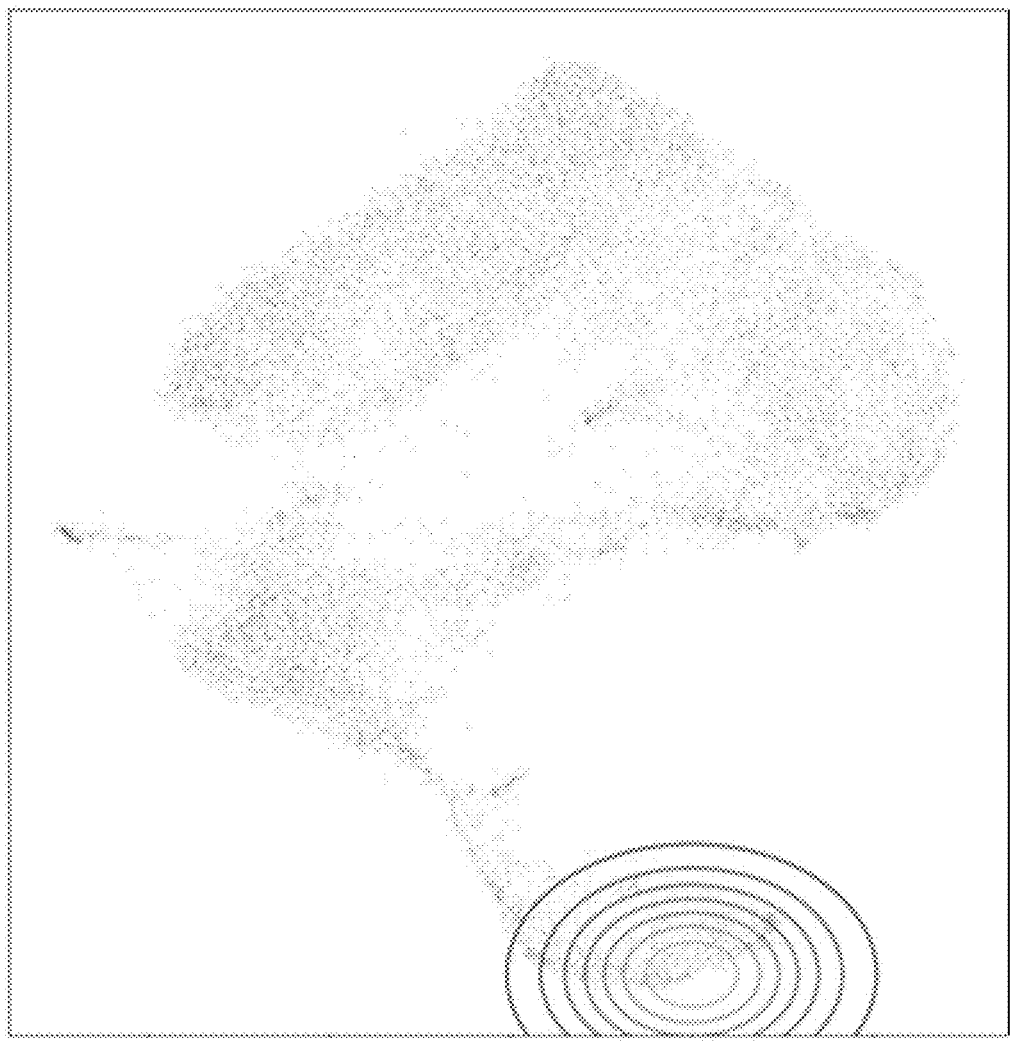
FIG. 21 illustrates a region of a state space visualization highlighted using a visualization tool, according to an embodiment.

Such a visualization tool above allows users to interactively explore their brain state space, and develop an understanding of which parts of the brain model state space correspond to which internal brain states. Specific zones in the brain model state space may then be identified as desirable target zones that the user desires to achieve. For example, if a particular region of the state space is identified as corresponding to the state of transcendence, this region is highlighted using the visualization tool as illustrated in FIG. 21.

A target zone can be defined with the notion of gravity, such that points closest to the center of the zone are associated with the greatest pull, and the gravitational force decays with distance from the center. Specification of the target zones may be done interactively by the user based on exploration, or automatically via a supervised or semi-supervised machine learning approach that leverages large scale databases of annotated meditation or sleep data.

Figure 22:
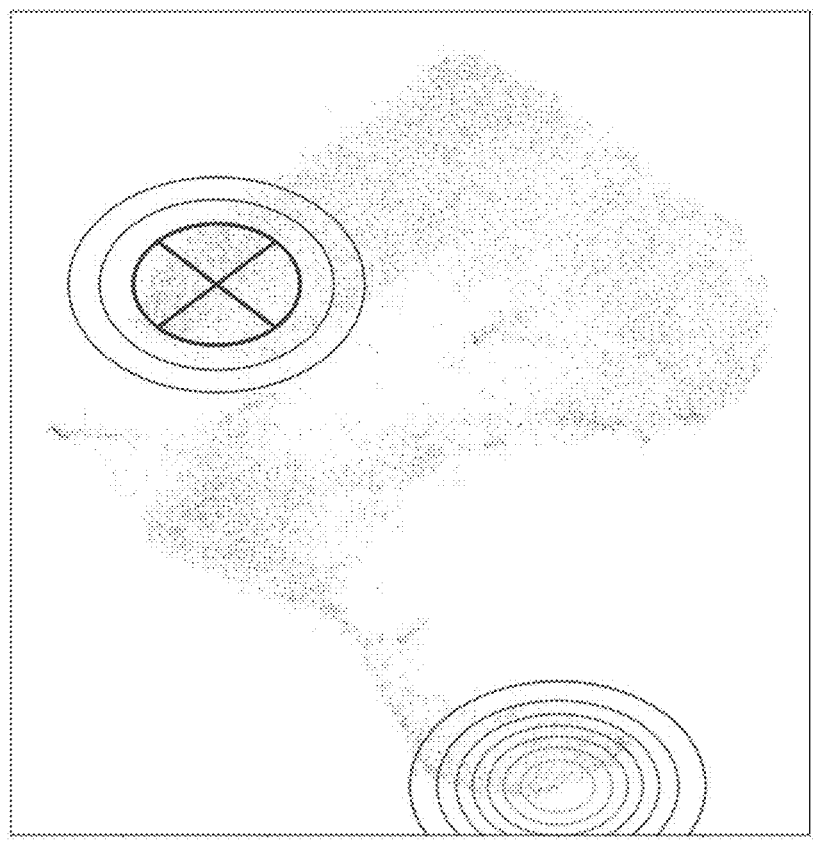
FIG. 22 illustrates another region of the state space visualization highlighted using a visualization tool, according to an embodiment.

In addition to target zones that the users desire to achieve, zones to be avoided can also be specified in a similar fashion as above. For example, if a user identifies a particular region of the brain state map corresponding to a distracted brain state, this could be defined as a region of the space that the user wishes to avoid. In the context of sleep, the user may define nocturnal arousals as undesirable with the aim to sleep soundly through the night. This is illustrated, for example, with an undesirable region highlighted in FIG. 22.

Given the defined regions for desirable and undesirable brain states, a user can be provided with real-time biofeedback that encourages progression towards the desirable zones, and discourages approaching the undesirable zones. For example, during a meditation experience, feedback may be provided by increasing the amplitude or frequency of occurrence of pleasing sounds when the user's brain model state navigates near to the target zone for compassion. When the user's state approaches a zone corresponding to a distracted state, the system could play a soft sound to alert the user to their state of distraction. As another example, when the user approaches a nocturnal awakening during sleep, gentle music, or a soothing voice could be played to discourage the user from awakening into a state of anxiety. In addition to audio feedback, other forms of bio-feedback such as scent-based or visual stimuli could also be incorporated as part of the system.

Figure 23:
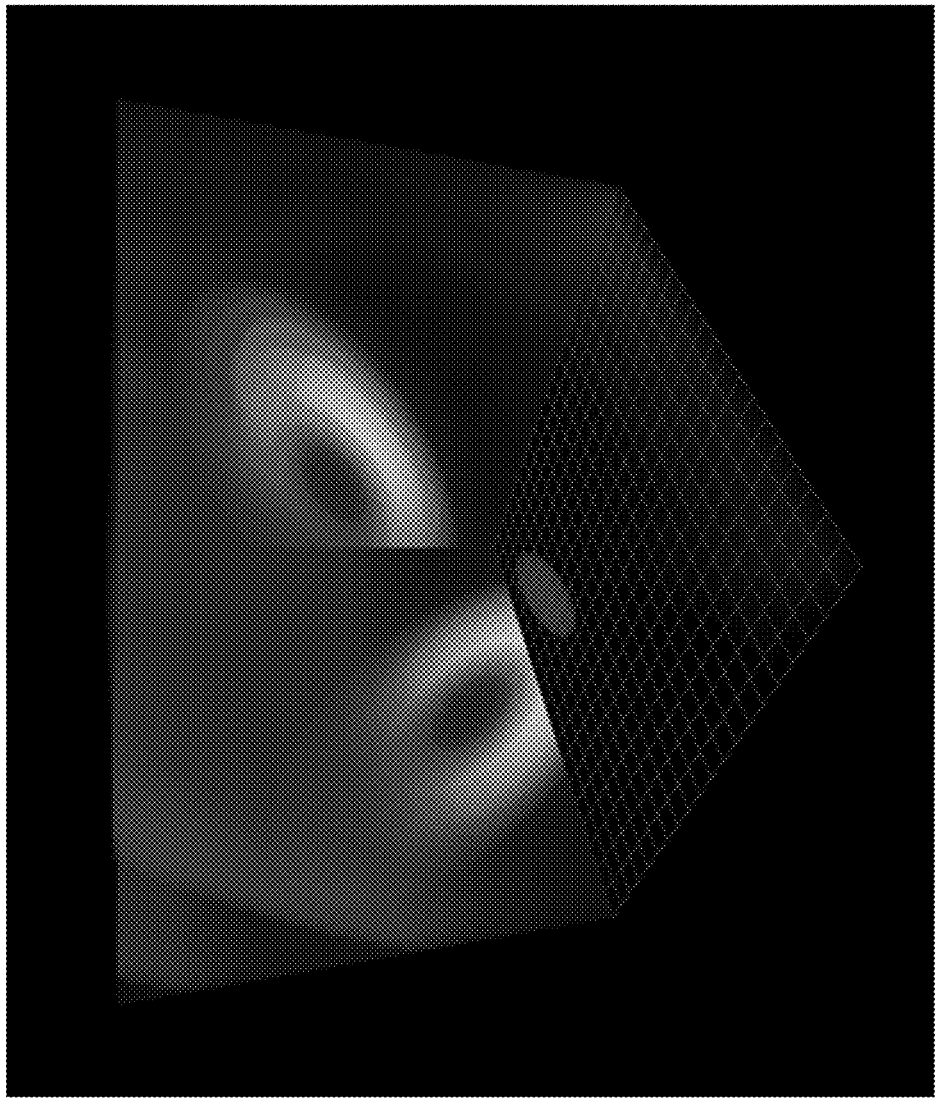
FIG. 23 illustrates a shared state space between users as an intersection of brain models, according to an embodiment.

Experiences can also be built for multiple users by leveraging multiple brain models. These can be built based on brain models pre-defined by each of the users, or by mutually exploring a joint brain model space, as shown for example in FIG. 23. FIG. 23 illustrates a shared state space between users as an intersection of brain models, according to an embodiment. For the first case, an example is provided in the context of a meditation experience. Users A and B first explore their respective brain models and determine target states, for example both users may specify target zones as a state of focused attention, or undesirable zones corresponding to states of distraction. During the shared experience, real-time audio feedback is played to both users, consisting of one sound source for each user (as in the single user experience), and another sound source that provides positive reinforcement played as both users approach their respective target zones. A state of mutual resonance occurs when both users remain in the target zones.

For mutual exploration of a joint model space, a single combined model is learned for both users. The exploration can then done by both users together, with target zones encoding the space of joint states. For example a target state might be when both users are in a state of relaxation together. The mutual space would also encode undesirable joint states that the users may wish to avoid such as states of conflict, that could alert the users to the potential conflict before it has the chance to set in.

Figure 24:
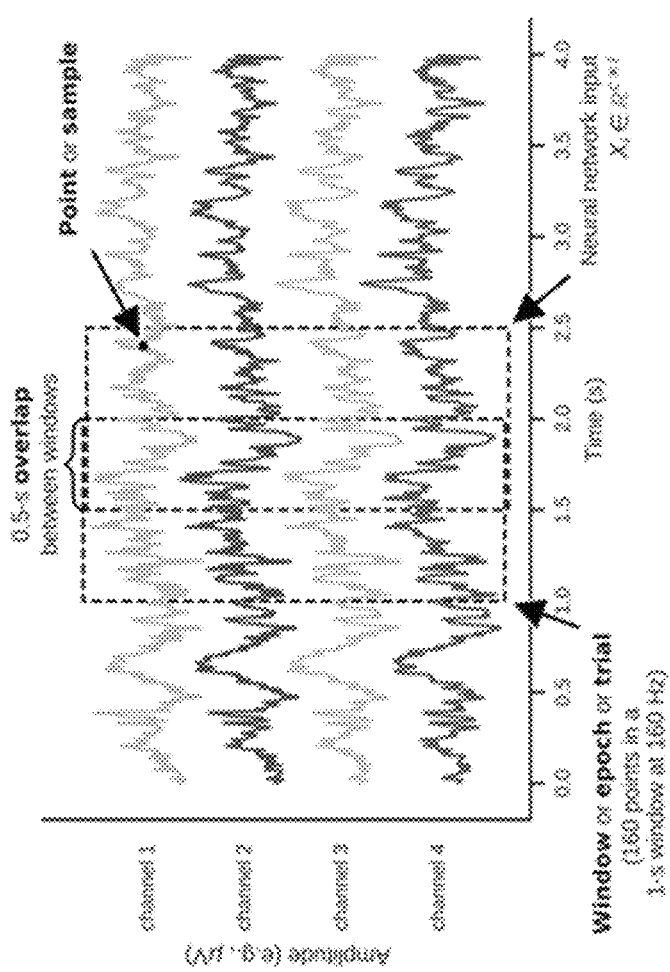
FIG. 24 illustrates model input of a multi-channel window of raw EEG signals, according to an embodiment.
Figure 25:
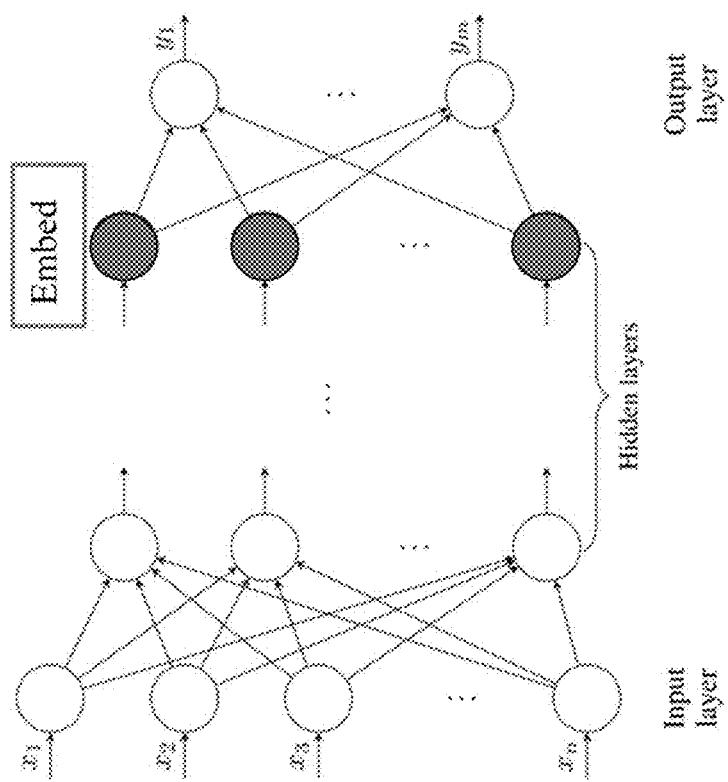
FIG. 25 illustrates an example neural network brain state model, according to an embodiment.

An example state space-based brain model is presented as a neural network approach with a latent embedded representation. The model takes as input a window of EEG samples, as shown for example in FIG. 24, and consists of a hierarchical composition of functional layers, as shown for example in FIG. 25. FIG. 24 illustrates example model input of a multi-channel window of raw EEG signals. FIG. 25 illustrates an example neural network brain state model.

Training of the model can be done in a supervised, semi-supervised, self-supervised, or unsupervised fashion, with a set of different loss functions. For example, for the meditation experience, a compositional unsupervised model trained on a large scale database of meditation data, such that the underlying compositional structure of the various stages of typical meditation sessions may be teased apart by the model. In the context of sleep, the model could be trained in a supervised fashion based on expert annotated sleep stages, such that the internal state space learns to reflect the breadth of possible sleep states of an entire population.

Figure 5A:
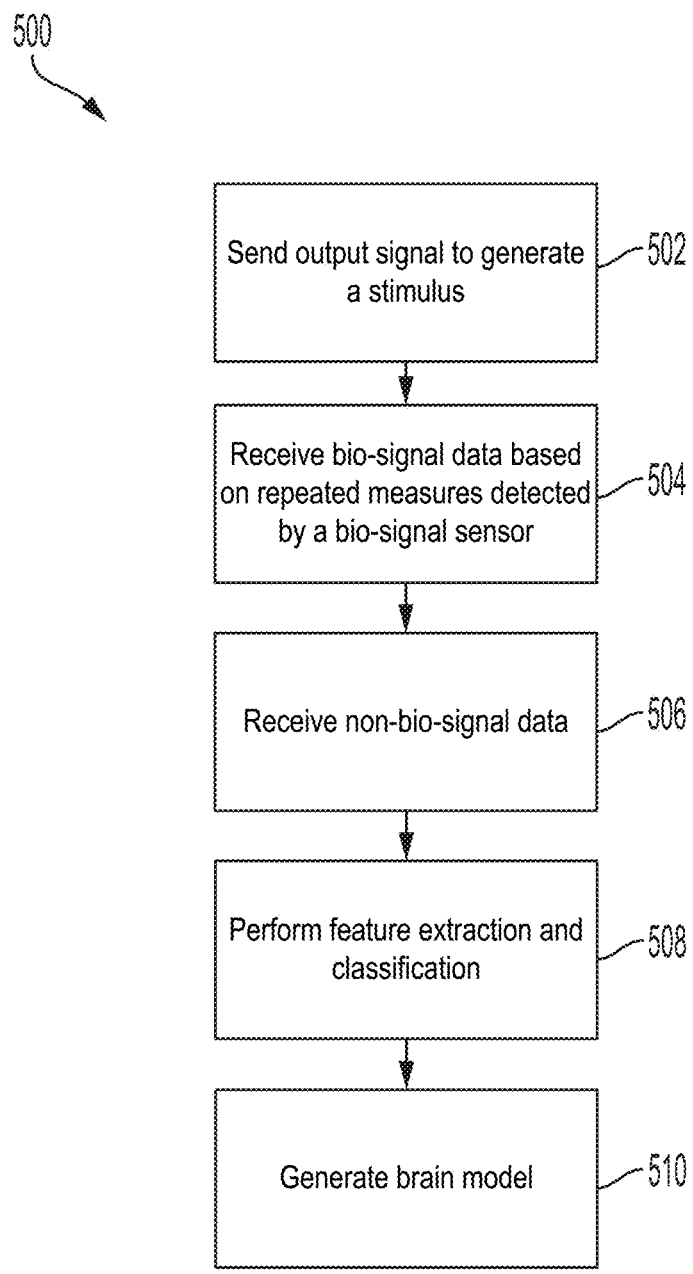
FIG. 5A illustrates a flow chart of a method for generating a brain model, according to an embodiment.

FIG. 5A illustrates a method 500 for generating a brain model, according to an embodiment. Blocks 502 to 510 may be performed by processor(s) 210. The steps are provided for illustrative purposes. Variations of the steps, omission or substitution of various steps, or additional steps may be considered.

At block 502, data collector 402 sends an output signal to generate a stimulus.

At block 504, data collector 402 receives bio-signal data based on repeated measures detected by a bio-signal sensor such as sensor 112.

In some embodiments, other data is received for time synchronization of the bio-signal data.

At block 506, data collector 402 receives non-bio-signal data.

At block 508, data processor 404 performs feature extraction and classification.

At block 510, brain model generator 406 generates a brain model.

It should be understood that the blocks may be performed in a different sequence or in an interleaved or iterative manner.

Figure 5B:
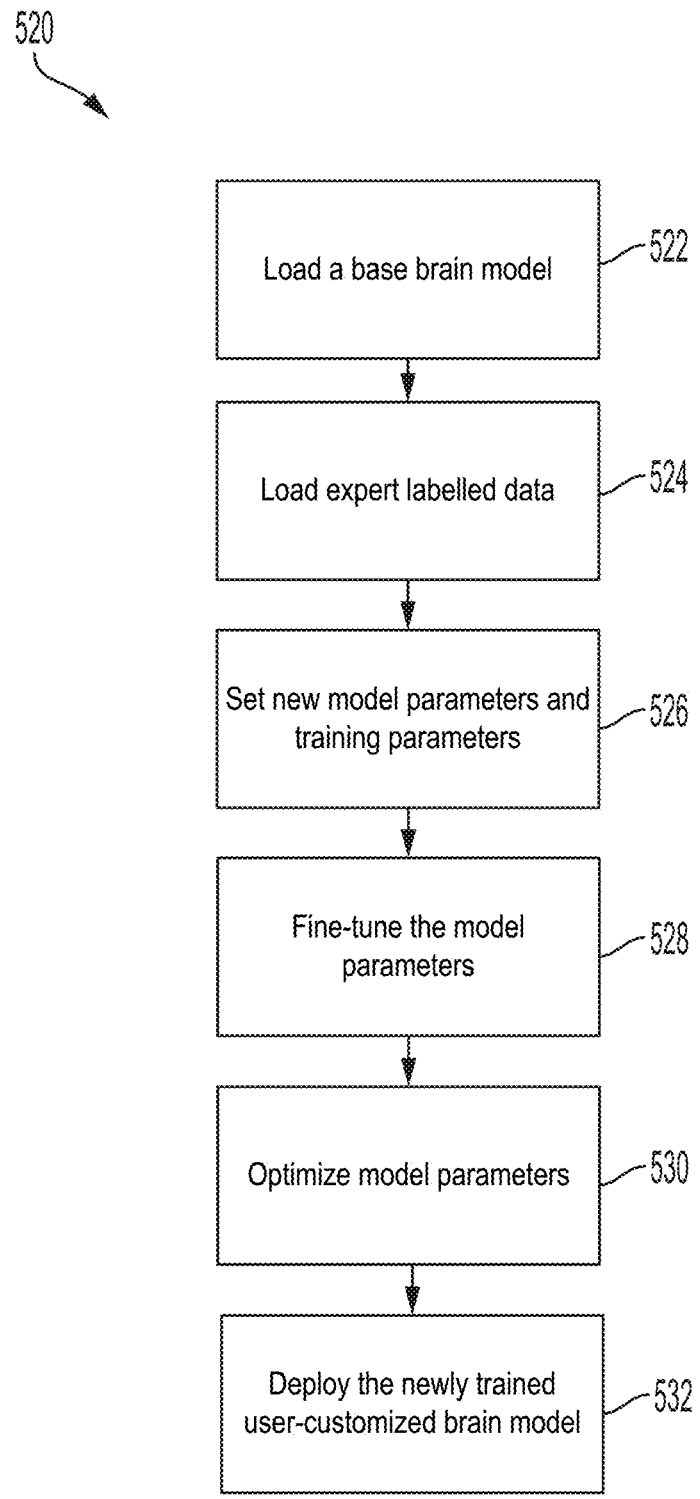
FIG. 5B illustrates flow chart of a method for model customization of a convolutional neural network (CNN) brain model, according to an embodiment.

FIG. 5B illustrates a method 520 for model customization (for example, fine-tuning or transfer-learning) of a convolutional neural network (CNN) brain model, such as the architecture illustrated in FIG. 14, for example, for sleep state prediction, according to an embodiment. Blocks 522 to 532 may be performed by processor(s) 210. The steps are provided for illustrative purposes. Variations of the steps, omission or substitution of various steps, or additional steps may be considered.

At block 522, a current base model is loaded.

At block 524, expert labelled data used for fine-tuning/user-customization is loaded.

At block 526, new model parameters and training parameters are set.

At block 528, the model generator is invoked to fine-tune the model parameters.

At block 530, the model parameters are optimized.

At block 532, the newly trained user-customized brain model is deployed.

It should be understood that the blocks may be performed in a different sequence or in an interleaved or iterative manner.

In an example of method 520 for model customization for sleep state prediction, method 520 includes the following steps:

Load the current base sleep state prediction model ("sCNN").

Load the newly labelled sleep data annotated by the sleep expert using the dashboard.

Set new sCNN training parameters such as learning rate, batch size, number of epochs, optimization algorithm parameters. Typically a learning rate smaller than the original learning rate is applied while fine tuning the model.

Start training on the new training data. In this step, based on the model's requirement, the weights of certain layers of the sCNN can be fixed/retained from the base model and the weights of certain other layers are modified/updated. Algorithms such as the Stochastic Gradient Descent can be used in this process.

Optimize the model parameters based on a validation set.

Deploy the newly trained sleep state prediction model—sCNN

Conveniently, embodiments herein may improve brain modelling and improve user experience. This, in use with brain sensors to obtain brain bio-signal, EEG, may make the user experience more customized and better for a user. For example, brain modelling techniques as disclosed herein can be used for differential diagnosis and/or adjunct therapy, such as by using a population model and an individual model (which can vary longitudinally over the course of treatment with the collection of additional inputs).

Figure 26:
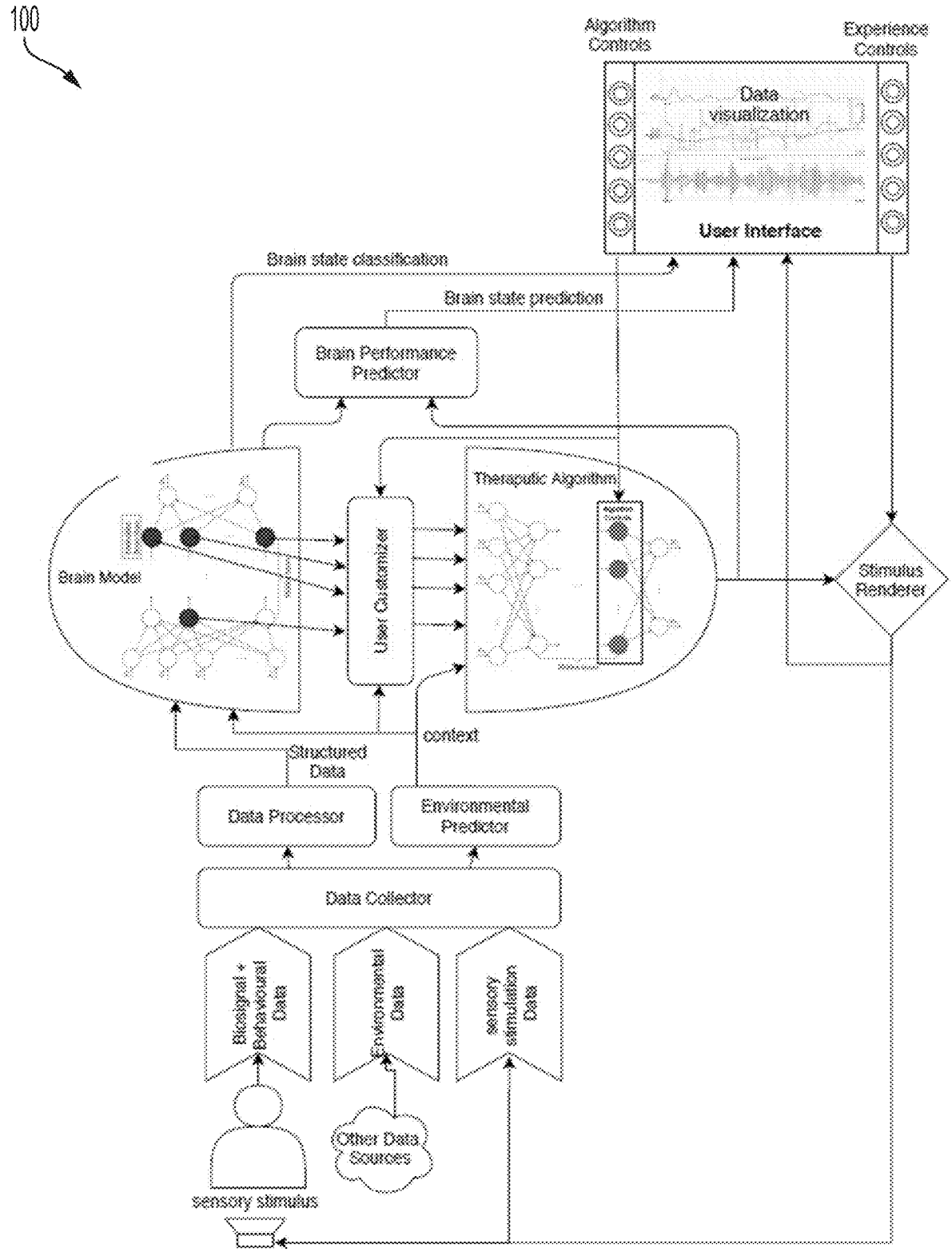
FIG. 26 is a schematic diagram of a system for brain modelling, according to an embodiment.

An embodiment of brain modelling system 100 is illustrated in FIG. 26. As shown, a Brain Model can be created and used as part of a feedback model, for example to generate feedback or output stimulus for a user, or a therapeutic application that may be based on a goal for a user's brain state, such as a therapeutic goal or emotional target. In this case an algorithm is used to interpret the current and prior states of the users brain and behaviour via state estimates provided by the brain model. These state estimates interact with the algorithm to determine the stimulus created for the user in the next time step. Changes in the user's brain state as a result of the interaction between user and the algorithm provides feedback, such as a stimulus, or therapeutic action.

An example algorithm is a mapping from a low dimensional representation of the user's brain state to volume multipliers on a set of pre-selected sounds that will be audible to the user. The user or a practitioner would have access to controls to modify the sounds samples or how they are mixed together, or specific parameters that affect the mapping in useful ways. These controls are applied to the Stimulus Render, which is responsible for taking the output of the therapeutic algorithm and applies any additional processes that are required to produce a stimulus for the user to experience.

These controls are typically presented in a User Interface that provides other information related to the user's brain state, expected brain performance, salient details of the algorithm such as the prior and future state in a treatment protocol, and rendering of the effect of the changes of the controls on the experience. The Brain Model, the Brain Performance Predictor and Therapeutic Algorithm include low dimensional outputs such that they can be rendered on a screen or in VR and interpreted easily by a human. An example control for the algorithm function would be to change the shape of an activation function that governs how a particular dimension of the user's brain state is mapped to the intensity of a particular sound frequency and color frequency that the user would subjected to via a sensory stimulus interface such as a speaker and a visual display.

Data in the system is aggregated by the Data Collector. This component receives data from all available sources, including the user's biosignal and behaviour data acquired by physical devices such as an EEG, PPG, ECG, touch sensors, cameras, microphones, movement sensors, light sensors, temperature sensors, and the like. Environmental data can include data such as barometric pressure, location, time of day, user activity, health data, calendars, and the like. Sensor stimulus data including raw and feature based information on the stimulus the therapeutic algorithm has created for the user to experience. The Data Collector time synchronizes the data, generates events related to data availability and makes data available to other processes via an interface that enables other processes to query what data is available, receive particular components of the data, particular times or time ranges of data, sensor configuration data.

The Data Processor does pre-processing and formatting of the data to make it appropriate as an input to the brain model algorithm. Example pre-processing includes removing AC-line noise from electrophysiological measures, spectral whitening, data coordinate transformations to compensate device and configuration variations.

The Environmental predictor provides an estimate of the user's context that is relevant to the brain model and the therapeutic algorithm. The context is also provided to the User Customizer. The User Customizer tunes/maps of relevant components of an individual's brain model to a therapeutic algorithm. For example, this calibration may involve the user engaging in different tasks such as engaging in a cognitive task or relaxing, to set thresholds in the therapeutic algorithm. Sensory stimulus may also part of the contextual data. For example in the case of the brain model producing estimates of an event related response to a stimulus, the brain model, the user customizer and therapeutic algorithm all need to know when the stimulus is happening vs not, to enable configuration of the algorithms to process the stimulus+response, and map the individuals response to the range and orientation of the input expected by the therapeutic algorithm.

The Brain Model is an algorithm that encodes information about the user's brain, bio-signal, and behavioural information such that classification of the user's state and predictions of the user's next state can be made. The brain model can take many forms. One example is a histogram of computed features such as a histogram of EEG powers in different frequency ranges. And a scoring algorithm that estimates the probability of the user's current brain data given the context using the histogram as an estimate of a probability distribution. Neural networks provide a much more powerful brain model, and may be trained in unsupervised or semi-supervised fashion using the data collected by the system, leveraging the Structured Data, Context, Data Store, Brain Model Store, and the Brain Model Generator. Expert or other sources of labelled data allow for supervised learning of parts of, or all of the Brain Model NN, through techniques such as Back Propagation.

Useful neural network (NN) architectures include auto-encoders, Convolutional Neural Net, RNN, LSTM, and other suitable variants.

A large database user data such as EEG data is used to pre-train Brain Models, such that in practice a user can have a useful Brain Model with a reasonable amount of use of the systems. Generative adversarial networks (GANs) can be used to train the system. Training of the brain model can be enhanced by using a GAN framework using a large database of user data to create the discriminator. The generative aspect of the brain model is effective for de-noising, interpolation and simulation. The Brain Model and Therapeutic Algorithm may be trained in a GAN framework, where the therapeutic algorithm is adapted to produce target brain and behavioural responses.

In some embodiments, the Brain Model Generator can be a neural network that is trained through back propagation, but may also function in simpler forms such as a matrix transformation. The User Customizer uses a pre-trained Brain Model and based on the user's context adapts relevant components of an individual's brain model to the therapeutic algorithm. Reinforcement learning based methods can also be leveraged to develop the Therapeutic Algorithm framework, wherein different therapeutic interventions can be simulated to derive novel treatment strategies.

Feedback models, or in an example, Therapeutic Algorithms (TA), may take the output of a neural network such as a classification, for example the Brain Model NN may classify if a user is Awake, in a REM, N1, N2, N3 stage of sleep. The TA may also use outputs from nodes intermediate (hidden layers) of the network. Training of the Brain Model creates a hierarchical representation of structure in the brain, bio-signal and behavioural data. Exploration of this structure by influencing or examining the activations of nodes or entire layers in the network, can yield insight into TAs that might be valuable for driving user outcomes. This exploration may be undertaken by a user or clinician through a set of controls and a user interface. The exploration is often done in the context of an existing TA such that the experience of the user is controlled for. In this case the User Customizer is reconfigured using controls available in the User Interface. The exploration may also be done algorithmically such as through a GAN framework. This is an important aspect as it can yield entirely new data driven techniques that may be tested with user's for efficacy evaluation. These new crowd tested algorithms also serve to create more data, stored in the Data Store to train Brain Model Networks and create new therapeutic salient Brain Model classification outputs.

One view of a TA is to create a stimulus that will elicit a desired response from the user. When the stimulus is received by the user, they respond to the stimulus and produce brain and behaviour data. The Brain Model interprets this brain and behaviour data along with the context data (which includes the stimulus) and produces a prediction of the user's state. Based on the difference between Brain Model's Brain state classification and the Brain Performance Predictor's brain state classification, the TA can adapt the stimulus based upon a protocol in order to track and reinforce a desired brain response.

An expert might design a protocol (such as an adaptive guided meditation) that involves adapting the stimulus to the achieved brain response. These expert protocols can be used as starting points in an optimization process to improve the therapeutic algorithm. Improvements are validated by running the system with human users, or by using a Brain Model that has been trained on a large quantity of data to reproduce brain state estimates from the context data alone. Another way creating new treatment algorithms is to user random protocols or random treatment variations as starting points to discover new methods of achieving a desired brain response.

As an example of how therapeutic algorithms may be improved using machine learning, Model-based deep reinforcement learning can be used for an adaptive guided meditation practice.

The anatomy of guiding prose has been a creative pursuit for experts to optimize a user's meditation or help individuals go to sleep more easily. This system provides functionality to automatically adapt to and generate go-to-sleep meditation experiences for our Muse users. There are three essential components in this system: environment, agent and policy. The environment is the combination of a human user and their associated brain model, and from the perspective of the therapeutic algorithm, can often be simplified as a set of evoked bio-signal responses from a stimulus to a human user (in this case guiding prose). This environment is essentially a set of rules in our system that defines what expected outcome might happen given an input. The agent is a smart, adaptive deep neural network that has an option to periodically pick a stimulus (auditory or otherwise) to nudge the user on a pre-defined path of success. The policy is a framework (or a truth table) that defines the reward or penalty term for the agent at the end of a pre-defined epoch. Together the policy and agent form the Therapeutic Algorithm.

In this framework, the voice guided experience leverages the massive amount of brain data and guided meditation and sleep inducement content from experts which allows a dictionary of potential stimuli for the agent and a policy network to be built that defines success metrics (often collaboratively with the user using the User Interface). From the repository of guided meditation content, a vast choice of auditory input has been developed that has been crafted by experts available for the agent to choose from. The brain model developed in the aforementioned training procedure maps the evoked bio-signal response to guided voice content on a word-by-word, sentence, paragraph and across other linguistic and natural language processing measures. Billions of minutes of bio-signal data across hundreds of thousands of users was used to develop a Brain Model. One example of the policy gradient for this agent is driving the user to a state of higher alpha band power and lesser alpha variance. The policy gradient also has time based reward/penalty terms. For example, the reward for the agent increases on a geometric progression if the user stays in a desired physiological state (for instance, higher alpha band-power, lower alpha variance).

Of course, the above described embodiments are intended to be illustrative only and in no way limiting. The described embodiments are susceptible to many modifications of form, arrangement of parts, details and order of operation. The disclosure is intended to encompass all such modification within its scope.

What is claimed is:

1. A computer-implemented method for brain modelling, the method comprising:
    receiving time-coded bio-signal data associated with a user from a bio-signal sensor;
    receiving time-coded stimulus event data;
    projecting the time-coded bio-signal data into a lower dimensioned feature space;
    extracting features from the lower dimensioned feature space that correspond to time codes of the time-coded stimulus event data to identify a brain response;
    generating a training data set for the brain response using the features;
    generating a brain model by transfer learning from one or more similar users by:
        comparing attributes of users to identify the one or more similar users;
        pooling data of the one or more similar users stored in a memory; and
        training the brain model from a base brain model using the pooled data using a processor that modifies parameters of the base brain model; and
    training the brain model using the training set using a processor that modifies the parameters of the brain model, the trained brain model unique to the user;
    generating a brain state prediction for the user output from the trained brain model, using a processor that accesses the trained brain model stored in the memory;
    inputting the brain state prediction to a feedback model to determine a feedback stimulus for the user, wherein the feedback model is associated with a target brain state; and
    causing the feedback stimulus to be provided to the user using a user effector.

2. The method of claim 1, further comprising comparing attributes of users to determine covariance, and based on the covariance, identifying the one or more similar users.

3. The method of claim 1, wherein the time-coded bio-signal data includes time-coded EEG data generated by repeated measures.

4. The method of claim 1, wherein the time-coded bio-signal data includes sensed event related potentials.

5. The method of claim 1, further comprising receiving non-bio-signal data, extracting features from the non-bio-signal data, and inputting the features of the non-bio-signal data to train the brain model.

6. The method of claim 5, wherein the brain model includes a representation of a relationship between the time-coded bio-signal data and the non-bio-signal data.

7. The method of claim 5, wherein the non-bio-signal data includes data representative of an environmental state of the user.

8. The method of claim 1, wherein the training of the brain model includes at least one of supervised, semi-supervised, unsupervised learning, or reinforcement learning.

9. The method of claim 1, wherein the brain model is at least one of a logistic regression, linear discriminant analysis, a random forest, gradient boosted trees, support vector machines, or ensemble learning.

10. The method of claim 1, wherein the brain model is a neural network.

11. The method of claim 10, wherein the brain model is trained by training parameters of the neural network.

12. The method of claim 10, wherein the neural network is at least one of or a combination of a convolutional neural network, recurrent neural network or long short term memory network.

13. The method of claim 1, wherein the feedback model is a neural network.

14. The method of claim 1, wherein the brain model is a generator and the feedback model is a discriminator in a generative adversarial network (GAN) framework.

15. The method of claim 1, wherein the feedback stimulus includes environmental effects.

16. The method of claim 15, further comprising receiving additional bio-signal data associated with the feedback stimulus, and further training the brain model based at least in part on the additional bio-signal data.

17. The method of claim 1, further comprising determining a treatment protocol for the user based at least in part on the trained brain model and the feedback model.

18. A computer system comprising: a bio-signal sensor in communication with a computing device, the computing device including a processor and a memory in communication with the processor, the memory storing instructions that, when executed by the processor cause the processor to perform the method of claim 1.

19. A non-transitory computer readable medium comprising a computer readable memory storing computer executable instructions thereon that when executed by a computer cause the computer to perform the method of claim 1.

20. A system for brain modelling, the system comprising:
a client computing device;
a bio-signal sensor, wherein the bio-signal sensor is in communication with the client computing device;
a user effector, wherein the user effector is in communication with the client computing device;
a server comprising a memory storing a plurality of user brain models, wherein the server is in communication with the client computing device;
the client computing device configured to:
  generate time-coded bio-signal data associated with a user using the bio-signal sensor;
  generate time-coded stimulus event data;
  transmit the time-coded bio-signal data and the time-coded stimulus event data to the server;
the server configured to:
  receive the time-coded bio-signal data;
  receive the time-coded stimulus event data;
  project the time-coded bio-signal data into a lower dimensioned feature space;
  extract features from the lower dimensioned feature space that correspond to time codes of the time-coded stimulus event data to identify a brain response;
  generate a training data set for the brain response using the features;
  generate a brain model by transfer learning from one or more similar users by:
    comparing attributes of users to identify the one or more similar users;
    pooling data of the one or more similar users stored in the memory; and
    training the brain model from a base brain model using the pooled data by modifying the parameters of the base brain model; and
  train the brain model using the training set by modifying the parameters of the brain model, the trained brain model unique to the user;
at least one of the client computing device and the server configured to:
  generate a brain state prediction for the user output using the trained brain model; and
  determine a feedback stimulus for the user from the brain state prediction using a feedback model, wherein the feedback model is associated with a target brain state; and
the user effector configured to:
  provide the feedback stimulus to the user.

* * * * *